(12) United States Patent
Lee et al.

(10) Patent No.: US 7,703,454 B2
(45) Date of Patent: Apr. 27, 2010

(54) INHALER WITH BREATH ACTUATED DOSE COUNTER

(75) Inventors: James I-Che Lee, Sacramento, CA (US); Reza Saied, Sacramento, CA (US); Glen M. Thomson, Cirtus Heights, CA (US)

(73) Assignee: Vortran Medical Technology, Sacramento, CA (US)

( * ) Notice: Subject to any disclaimer, the term of this patent is extended or adjusted under 35 U.S.C. 154(b) by 934 days.

(21) Appl. No.: 10/888,445

(22) Filed: Jul. 9, 2004

(65) Prior Publication Data

US 2005/0011515 A1     Jan. 20, 2005

Related U.S. Application Data

(60) Provisional application No. 60/487,493, filed on Jul. 14, 2003.

(51) Int. Cl.
*A61M 15/00* (2006.01)

(52) U.S. Cl. .................................. 128/201.15

(58) Field of Classification Search ............ 128/200.23, 128/200.21, 203.15, 203.12, 202.22, 205.23, 128/203.1
See application file for complete search history.

(56) References Cited

U.S. PATENT DOCUMENTS

| | | | |
|---|---|---|---|
| 3,636,949 A | 1/1972 | Kropp | |
| 4,972,830 A * | 11/1990 | Wong et al. | 128/200.21 |
| 5,069,204 A | 12/1991 | Smith et al. | |
| 5,349,945 A | 9/1994 | Law et al. | |
| 5,447,150 A | 9/1995 | Bacon | |
| 5,511,540 A | 4/1996 | Bryant et al. | |
| 5,544,647 A * | 8/1996 | Jewett et al. | 128/200.23 |
| 5,564,414 A * | 10/1996 | Walker et al. | 128/200.23 |
| 5,894,841 A * | 4/1999 | Voges | 128/203.12 |
| 6,405,727 B1 | 6/2002 | Hearne et al. | |
| 6,701,917 B2 | 3/2004 | O'Leary | |
| 6,718,972 B2 | 4/2004 | O'Leary | |
| 6,866,038 B2 * | 3/2005 | Bacon | 128/200.23 |
| 2002/0078949 A1 | 6/2002 | O'Leary | |
| 2002/0104532 A1 | 8/2002 | Geert-Jensen et al. | |
| 2002/0195102 A1 | 12/2002 | Godfrey et al. | |
| 2003/0172927 A1 * | 9/2003 | Young et al. | 128/203.15 |
| 2003/0183225 A1 | 10/2003 | Knudsen | |
| 2004/0069301 A1 | 4/2004 | Bacon | |
| 2005/0028812 A1 * | 2/2005 | Djupesland | 128/200.21 |

FOREIGN PATENT DOCUMENTS

EP      0 308 524 A1    3/1989
WO      WO 93/24167     12/1993

* cited by examiner

*Primary Examiner*—Patricia Bianco
*Assistant Examiner*—O. H.
(74) *Attorney, Agent, or Firm*—John P. O'Banion

(57) ABSTRACT

A device is disclosed for dispensing a fluid supplied from an external fluid source. The device comprises a transducer adapted to receive a fluid from the fluid source, and a collapsible linkage coupling the transducer and the fluid source. The linkage has a collapsible joint inhibiting discharge of the fluid source when in a locked orientation. The device further comprises a movable member coupled to the linkage such that inhalation forces on the device cause the linkage to collapse thereby discharging the fluid from the fluid source. The device may further include a dose counter coupled to the fluid source for registering the amount of doses administered from the fluid source.

47 Claims, 33 Drawing Sheets

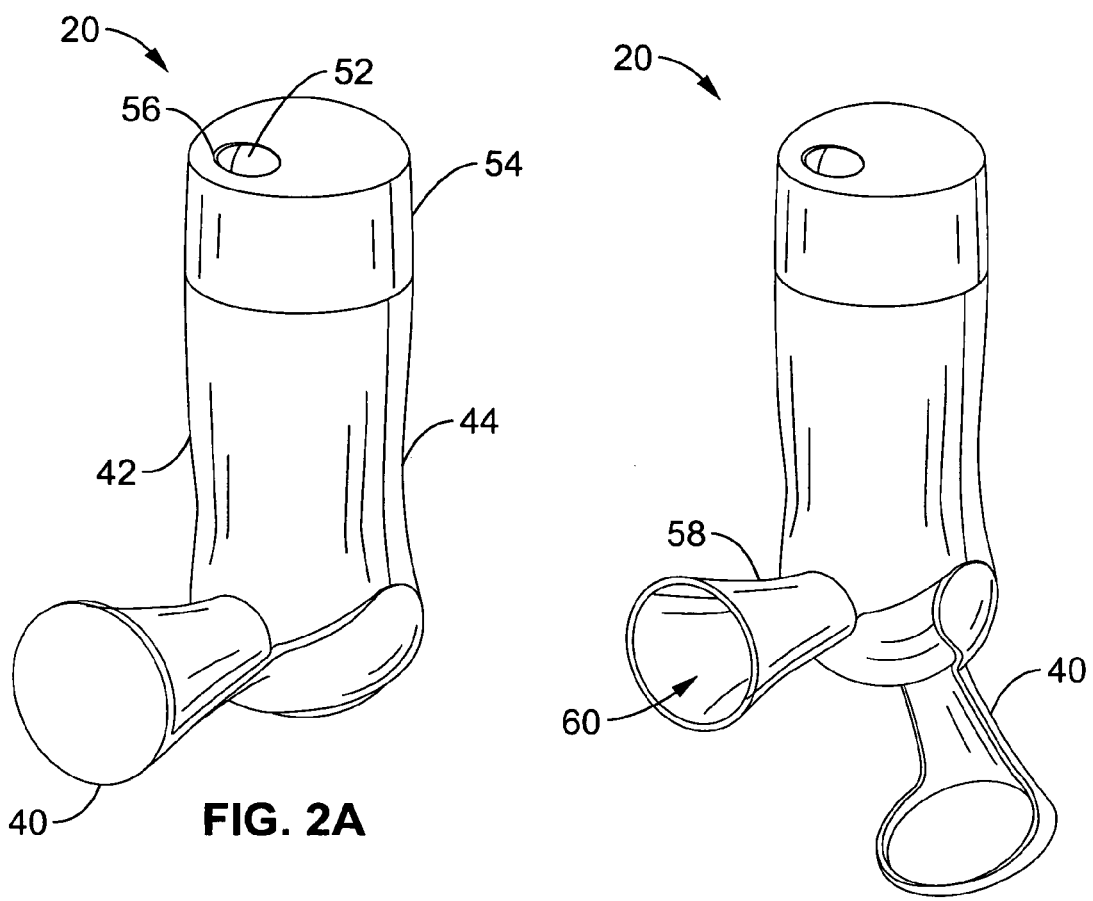
FIG. 2A
FIG. 2B
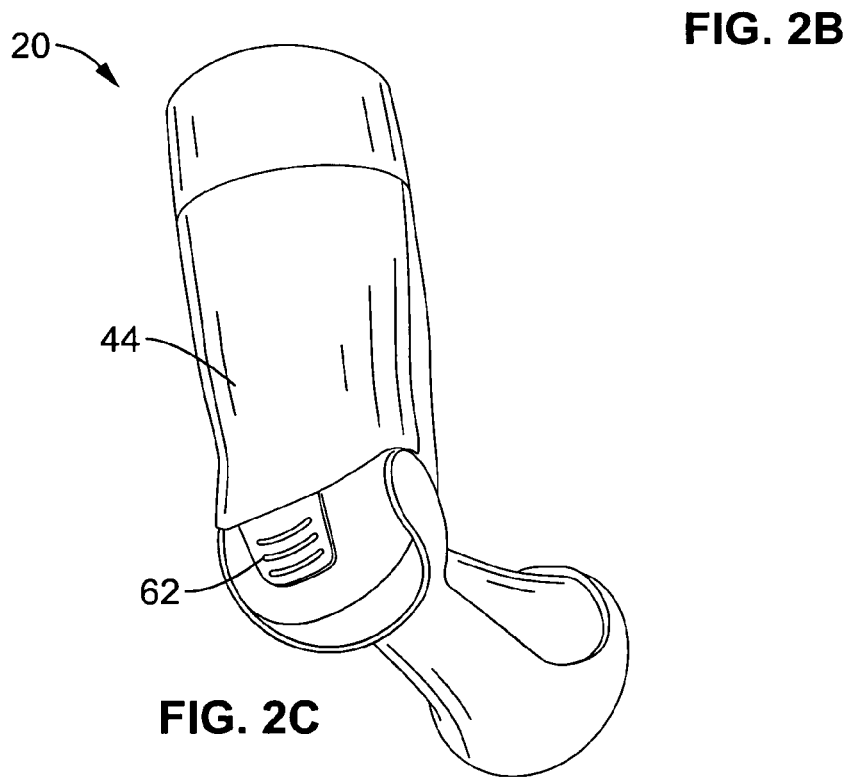
FIG. 2C

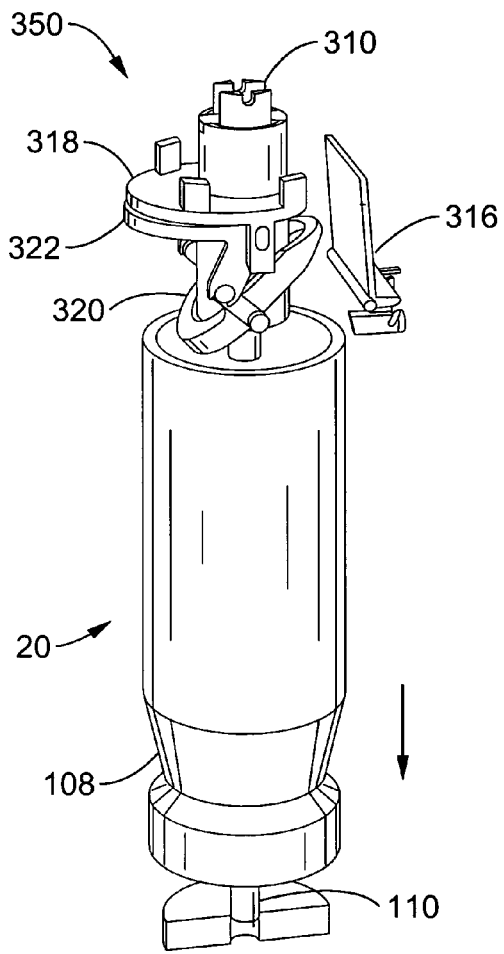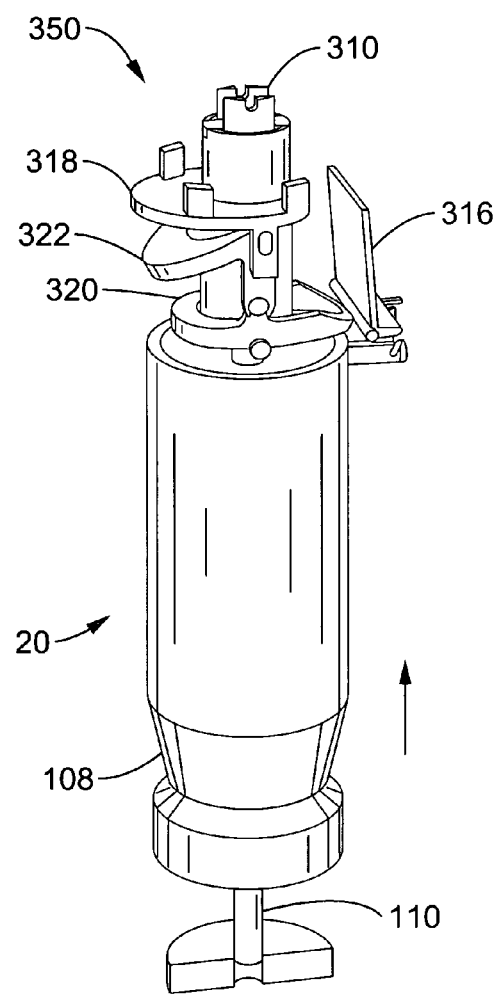
FIG. 16C
FIG. 16D

INHALER WITH BREATH ACTUATED DOSE COUNTER

CROSS-REFERENCE TO RELATED APPLICATIONS

This application claims priority from U.S. provisional application Ser. No. 60/487,493 filed on Jul. 14, 2003, the entirety of which is herein incorporated by reference. This application is related to application Ser. No. 11/299,307, filed Dec. 9, 2005, now U.S. Pat. No. 7,600,512.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the U.S. and of other countries. The owner of the copyright rights has no objection to the facsimile reproduction by anyone of the patent document or the patent disclosure, as it appears in the U.S. Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND OF THE INVENTION

1. Field of the Invention

This invention pertains generally to metered dose inhalers and more specifically, to a metered dose inhaler with a breath actuated delivery mechanism and dose counter.

2. Description of Related Art

Inhalers are commonly used to deliver a wide range of medicaments to the bronchial passages, lungs and bloodstream of the user. Typical inhalers hold a container of pressurized medicament and propellant that is actuatable, generally by compression, to deliver a dose of medicament through a mouthpiece to the patient.

It is generally desirable for the dose of medication to be dispensed at the same time that the patient inhales air to permit the majority of medication to enter the lung rather than the mouth or esophagus. A number of inhalers have been developed that use breath actuated devices to automatically initiate the discharge of the medicament from the container when the patient inhales. Many of these devices, such as U.S. Pat. No. 5,069,204 to Smith et al., use latching mechanisms that require a considerable amount of air pressure to release the medicament. These higher release pressures lead to difficulty of use, and discharge at non-optimal points in the patient's breath cycle.

It is therefore an object of the present invention to provide a breath-actuated inhaler having a controllable release mechanism that is sensitive to the inhalation forces of the user to provide synchronous air entrainment and medicament delivery. It is further an object of the present invention to provide a simple and reliable dose counter responsive to discharge of the medicament container.

BRIEF SUMMARY OF THE INVENTION

According to a first aspect of the invention, an apparatus is provided for dispensing a first fluid supplied from an external fluid source comprising a transducer adapted for receiving the first fluid from the fluid source, wherein translation of a portion of the fluid source along a first axis releases the first fluid into the transducer. The apparatus will generally have a loading member coupled to the fluid source to impose a biasing force to the fluid source along the first axis.

In all cases, the apparatus has a linkage coupling the transducer and the fluid source, the linkage having a collapsible joint inhibiting translation of the fluid source in the first axis when the collapsible joint is oriented in a first position, and allowing translation of the fluid source in the first axis when the collapsible joint is oriented in a second position. The apparatus further comprises a movable member coupled to the linkage, the moveable member responsive to an inhalation force exerted on the moveable member, the inhalation force causing the movable member to shift the collapsible joint from the first position to the second position, thereby allowing translation of a portion of the fluid source in the first axis from a stowed position to a discharge position to discharge the first fluid into the transducer.

In preferred embodiments, the transducer further comprises one or more vents to entrain the first fluid with a second fluid. Additionally, there may be a plug coupled to the transducer. Ideally, the plug is retained in a first chamber of the transducer and has a bluff surface such that the axis of the bluff surface is perpendicular to the first axis.

The apparatus of the present invention has an inhalation horn coupled to the transducer. The inhalation horn has a second chamber positioned along a second axis, wherein the second chamber is in communication with the first chamber via an outlet positioned at a first end of the second chamber. Suction on the inhalation horn by the user causes an inhalation force on the moveable member. In many embodiments, the second axis is perpendicular to the first axis. Generally, the second chamber has an internal cross section that increases from the first end to a second end forming an opening in the horn. In some embodiments, the internal cross section of the second chamber is parabolic.

Typically, the moveable member comprises a flap rotatably mounted to the transducer, wherein the flap rotates in response to the inhalation force. The flap is generally configured to rotate from a first orientation retaining the collapsible joint in the first position, to a second orientation allowing the collapsible joint to move to the second position as a result of the force applied in the first axis. Usually the device includes a flap spring coupled to the flap and the transducer to return the flap from the second orientation to the first orientation after the inhalation force has subsided.

In a preferred embodiment, the linkage comprises an upper link and a lower link, the upper link and the lower link rotatably attached to form the collapsible joint, a first end of the lower link rotatably housed in the transducer. A second end of the lower link is coupled to the flap and the mating surfaces of the lower link and the flap are configured so that the lower link contacts the flap to retain the collapsible joint in the first position when the flap is in the first orientation. When the flap is in the second orientation, the lower link is free to advance past the flap to allow the collapsible joint to move to the second position. In a preferred embodiment, a reset spring is coupled to the lower link to return the collapsible joint from the second position to the first position.

In some embodiments, a container holder is configured to receive a first end of the fluid source, wherein the container holder is coupled to the upper link. The container holder further comprises one or more protrusions.

Preferably, a dust cover is pivotably coupled to the transducer. The dust cover covers the horn opening in a first orientation, and allows access to the horn opening in a second orientation. In a preferred embodiment, the dust cover comprises one or more cams that are configured to contact the one or more protrusions on the container holder upon rotation of the dust cover from the second orientation to the first orientation, thereby advancing the container holder and fluid source from the discharge position to the stowed position.

In an alternative embodiment, the moveable member comprises a diaphragm mounted to the transducer, wherein a central portion of the diaphragm moves in response to the inhalation force. In this configuration, the collapsible joint is coupled to the central portion of the diaphragm, so that the inhalation force deflects the central portion of the diaphragm to orient the collapsible joint from the first position to the second position.

In another aspect of the invention, the apparatus comprises a dose counter coupled to the fluid source. Ideally, the dose counter is responsive to motion of the fluid source in the first axis to count each dose of fluid released from the fluid source.

In one embodiment, the dose counter further comprises a first wheel having a plurality of teeth along its perimeter, the plurality of teeth positioned to rotationally advance the first wheel in response to movement of the fluid source along the first axis. A second wheel positioned adjacent the first wheel, the second wheel having markings for indicating the number of doses discharged from the fluid source. The first wheel is preferably configured to engage the second wheel such that the second wheel rotates at a scaled movement in relation to the first wheel.

The apparatus may further comprise a sleeve configured to house a portion of the fluid source, wherein the sleeve has a protrusion that contacts the teeth of the first wheel to rotationally advance the first wheel as the fluid source is advanced in the first axis. The loading member may also have a spring coupled to the sleeve, wherein the spring provides a compressive force to the fluid source to bias the fluid source to move in the first axis.

In some embodiments, the apparatus may further have a manual release button. The button is coupled to the collapsible joint to manually shift the collapsible joint from the first position to the second position, thereby releasing the first fluid into the transducer.

In another aspect of the invention, an inhaler for dispensing metered doses of a medicament comprises a fluid source containing the medicament, wherein the fluid source has a cylindrical container having a nozzle located in line with a discharge axis of the container. The nozzle discharges the medicament when the container is advanced relative to the nozzle from a stowed position to a discharge position along the discharge axis. The inhaler further includes a transducer having a surface configured to engage the nozzle of the fluid source. The inhaler preferably has a loading member coupled to the container, the loading member imposing a biasing force to the container to discharge the container along the first axis. A linkage couples the transducer and the container, wherein the linkage has a collapsible joint inhibiting translation of the container in the first axis when the collapsible joint is oriented in a first position, and allowing translation of the container in the first axis when the collapsible joint is oriented in a second position. The inhaler also has a movable member coupled to the linkage, the moveable member responsive to an inhalation force, the inhalation force causing the movable member to shift the collapsible joint from the first position to the second position, thereby allowing translation of the container in the first axis from the stowed position to the discharge position to discharge the fluid into the transducer.

The moveable member comprises a flap rotatably mounted to the transducer, wherein the flap rotates in response to the inhalation force. The flap is configured to rotate from a first orientation retaining the collapsible joint in the first position, to a second orientation allowing the collapsible joint to move to the second position as a result of the force applied in the first axis.

The linkage preferably has an upper link and a lower link, the upper link and the lower link rotatably attached to form the collapsible joint, a first end of the lower link rotatably housed in the transducer. A container holder is configured to receive a first end of the container, wherein the container holder is coupled to the upper link. In some embodiments, the container holder further comprises one or more protrusions. A dust cover is pivotably coupled to the transducer, wherein the dust cover covers a horn opening in a first orientation, and allowing access to the horn opening in a second orientation. The dust cover may also have one or more cams configured to contact the one or more protrusions on the container holder. Upon rotation of the dust cover from the first orientation to the second orientation, the container holder and container are advanced from the discharge position to the stowed position.

In another aspect of the invention, a dose counter is coupled to the container, wherein the dose counter is responsive to motion of the container in the first axis to count each dose of fluid discharged from the fluid source. In one embodiment, the dose counter comprises a first wheel having a plurality of teeth along its perimeter, the plurality of teeth positioned to rotationally advance the first wheel in response to movement of the fluid source along the first axis, and a second wheel positioned adjacent the first wheel, the second wheel having markings for indicating the number of doses discharged from the fluid source. Preferably, the first wheel is configured to engage the second wheel such that the second wheel rotates at a scaled movement in relation to the first wheel.

In yet another aspect of the invention an inhaler for dispensing metered doses of a medicament comprises a fluid source containing the medicament. The fluid source has a nozzle and a container, wherein the nozzle discharges the medicament when the container is advanced relative to the nozzle from a stowed position to a discharge position along a first axis. The inhaler has a transducer having a surface configured to engage the nozzle of the fluid source and a loading member coupled to the container, the loading member imposing a force to the container to bias the container to discharge along the first axis.

The inhaler further has a means for collapsibly retaining the fluid source from translating along the first axis a means for releasably supporting the collapsible retaining means, wherein the releasable support means releases support of the collapsible retaining means in response to an inhalation force.

In many embodiments, the releasable support means has a first orientation retaining the collapsible retainer means in a first, locked position, and a second orientation allowing the retainer means to collapse to a second unlocked position, and wherein the inhalation force causes the releasable support means to shift from the first orientation to the second orientation, thereby allowing translation of the container in the first axis from the stowed position to the discharge position to discharge the fluid.

In another aspect of the invention, the inhaler also includes a means for counting the number of doses of dispensed medicament, wherein the counting means is responsive to the axial motion of the container. Preferably, the counting means is responsive to both the motion of the container from the stowed position to the discharged position, and the motion of the container from the discharged position back to the stowed position.

In many embodiments, the counting means comprises a gear means for translating the axial motion of the container into a corresponding radial motion, and a display means for displaying the number of doses based on the radial motion of the gear means. In preferred embodiments, the display means may be scaled with respect to the gear means to match the total dose count of the fluid source.

In yet another aspect of the invention, an inhaler for dispensing metered doses of a medicament comprises a fluid source comprising a cylindrical container having a nozzle located in line with a discharge axis of the container, wherein the nozzle discharges the medicament when the container is advanced relative to the nozzle along the discharge axis. A container sleeve is configured to house a portion of the container, the container sleeve having a protrusion extending outward radially from the container. The inhaler further comprises a first wheel having a plurality of teeth along its perimeter, the plurality of teeth positioned to rotationally advance the first wheel in response to contact from the protrusion on the container sleeve as the container sleeve and container advance in the discharge axis, wherein the rotation motion of the first wheel indicates the number of metered doses dispensed from the fluid source.

In a preferred embodiment, a second wheel is positioned adjacent the first wheel, the second wheel having markings for indicating the number of doses discharged from the fluid source, wherein the first wheel is configured to engage the second wheel such that the second wheel rotates at a scaled movement in relation to the first wheel. The first wheel has a plurality of engagement surfaces for engaging the second wheel, wherein the number of engagement surfaces varies the rate of the movement of the second wheel with respect to the first wheel.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

FIG. 1A is an exploded view of the upper portion and dose counter of an embodiment of the present invention FIG. 1B is an exploded view of the lower portion of the embodiment of FIG. 1A, including the release mechanism.

FIGS. 2A-C are perspective views of the exterior housing of the embodiment of the inhaler of FIGS. 1A-B in a fully assembled configuration.

Figure 5A:
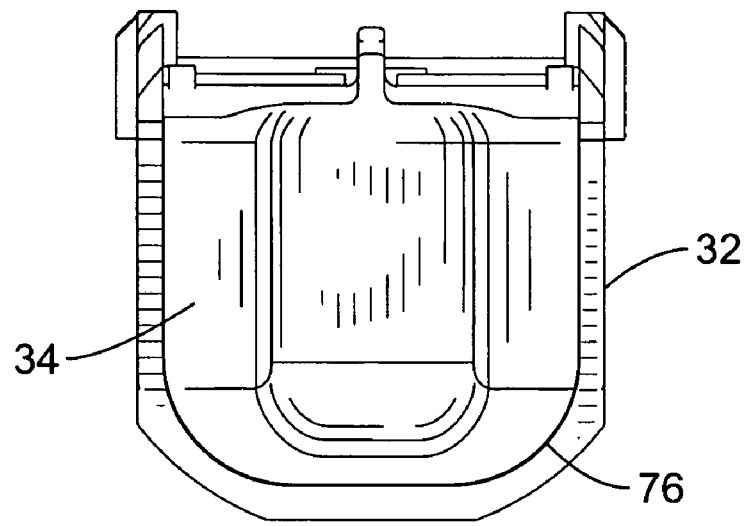
Figure 5B:
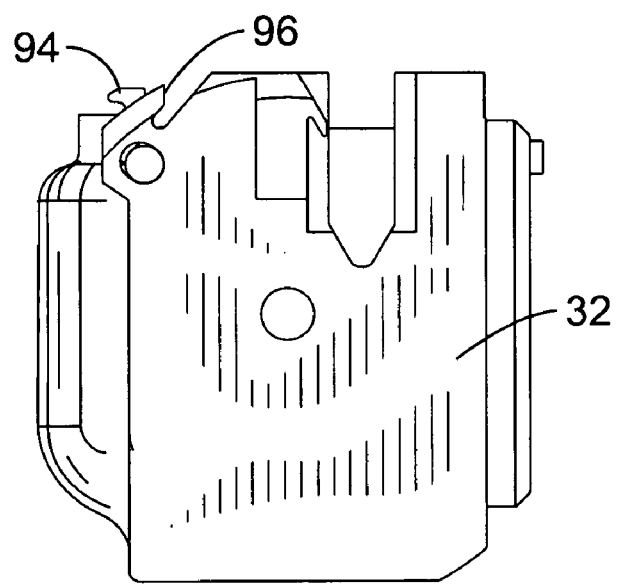

FIGS. 5A-B show schematic views of the flap and transducer of the present invention.

Figure 6A:
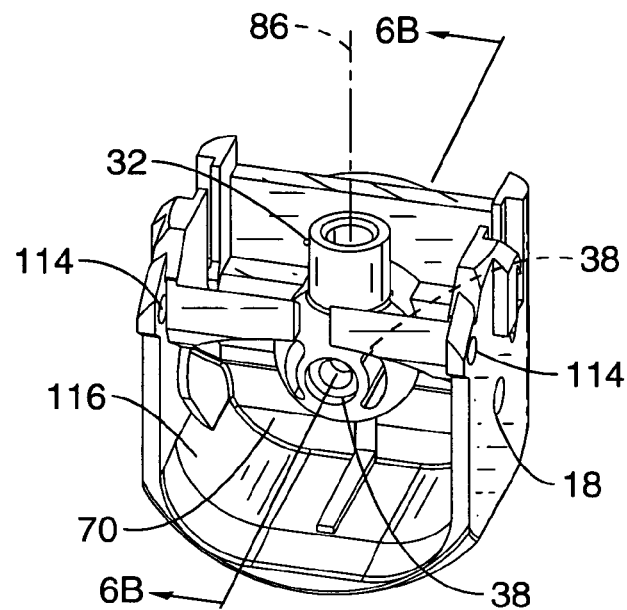

FIG. 6A is a perspective view of an embodiment of the transducer of the present invention.

Figure 6B:
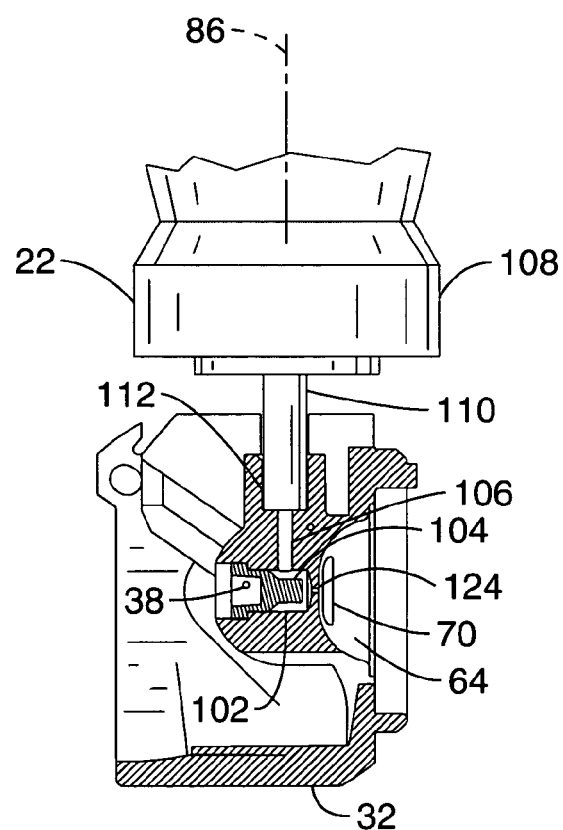

FIG. 6B illustrates a cross-sectional schematic view the transducer of FIG. 6A with the fluid source in a stowed configuration.

Figure 7A:
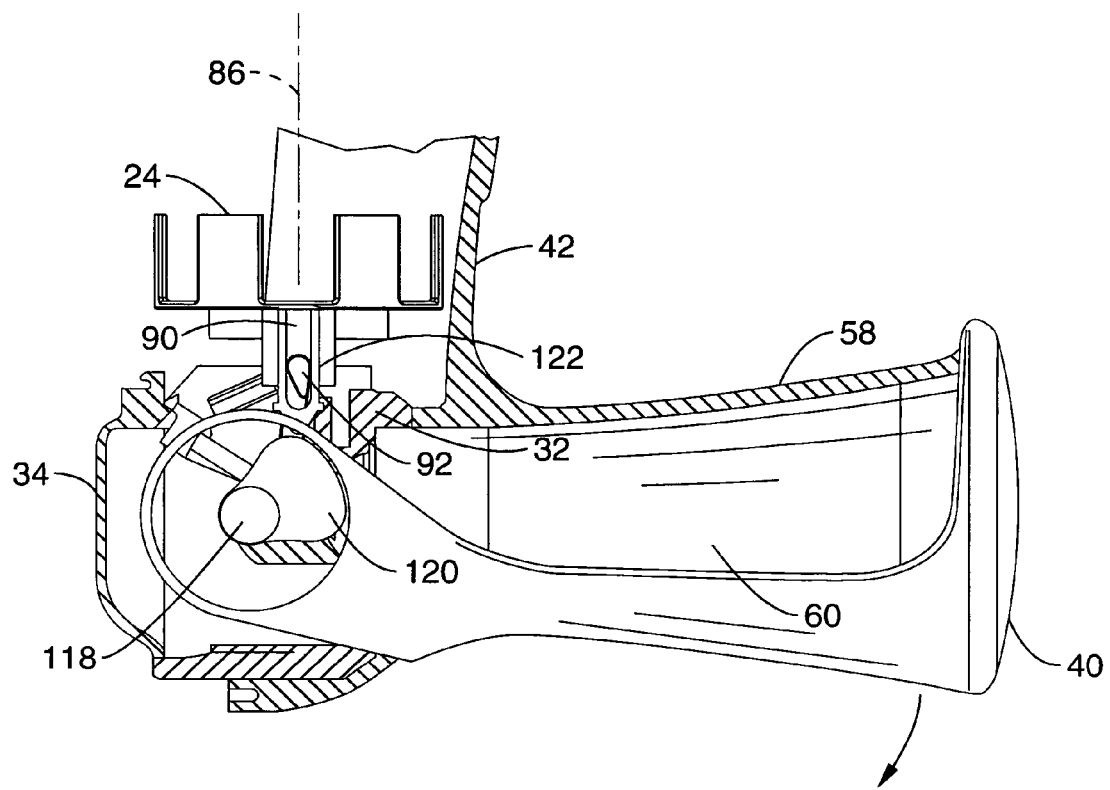

FIG. 7A is a cross-sectional view detailing the release mechanism of the present invention in a stowed configuration and the dust cover cut out to show the release mechanism.

Figure 7B:
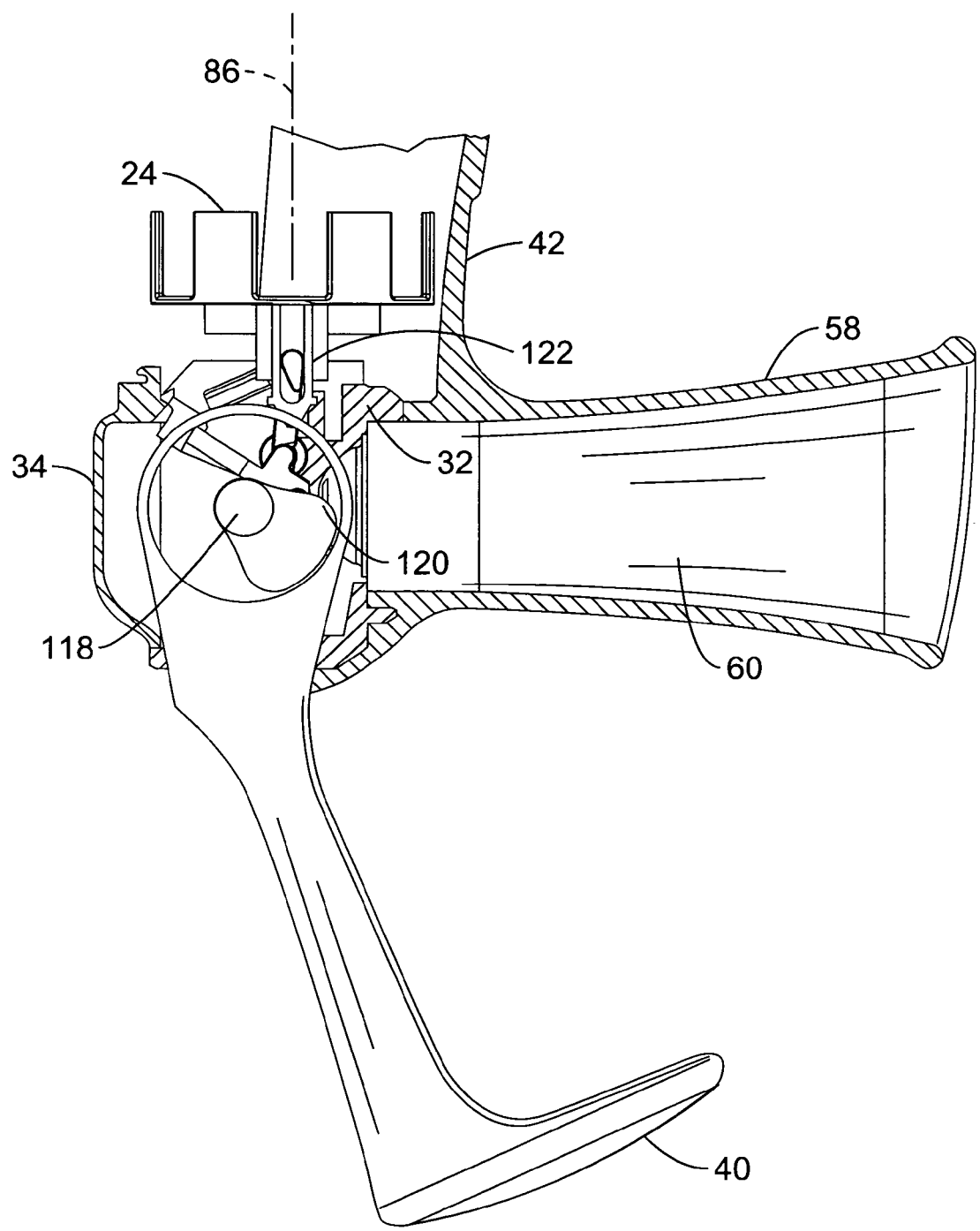

FIG. 7B illustrates the device of FIG. 7A with the dust cover rotated away from the horn and the release mechanism in the stowed configuration prior to breath actuation.

Figure 7C:
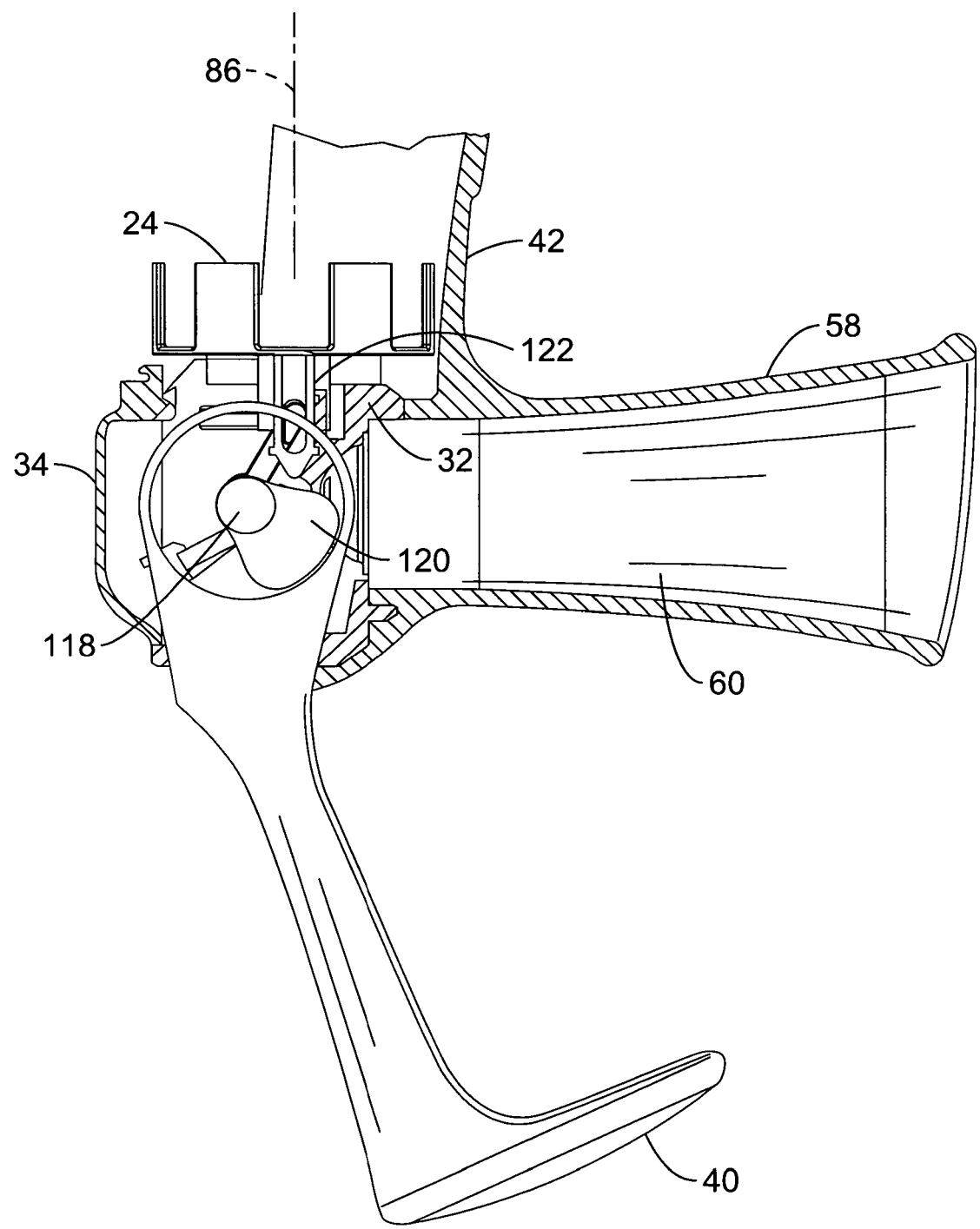

FIG. 7C illustrates the device of FIG. 7B with the release mechanism in the discharged configuration after breath actuation.

Figure 7D:
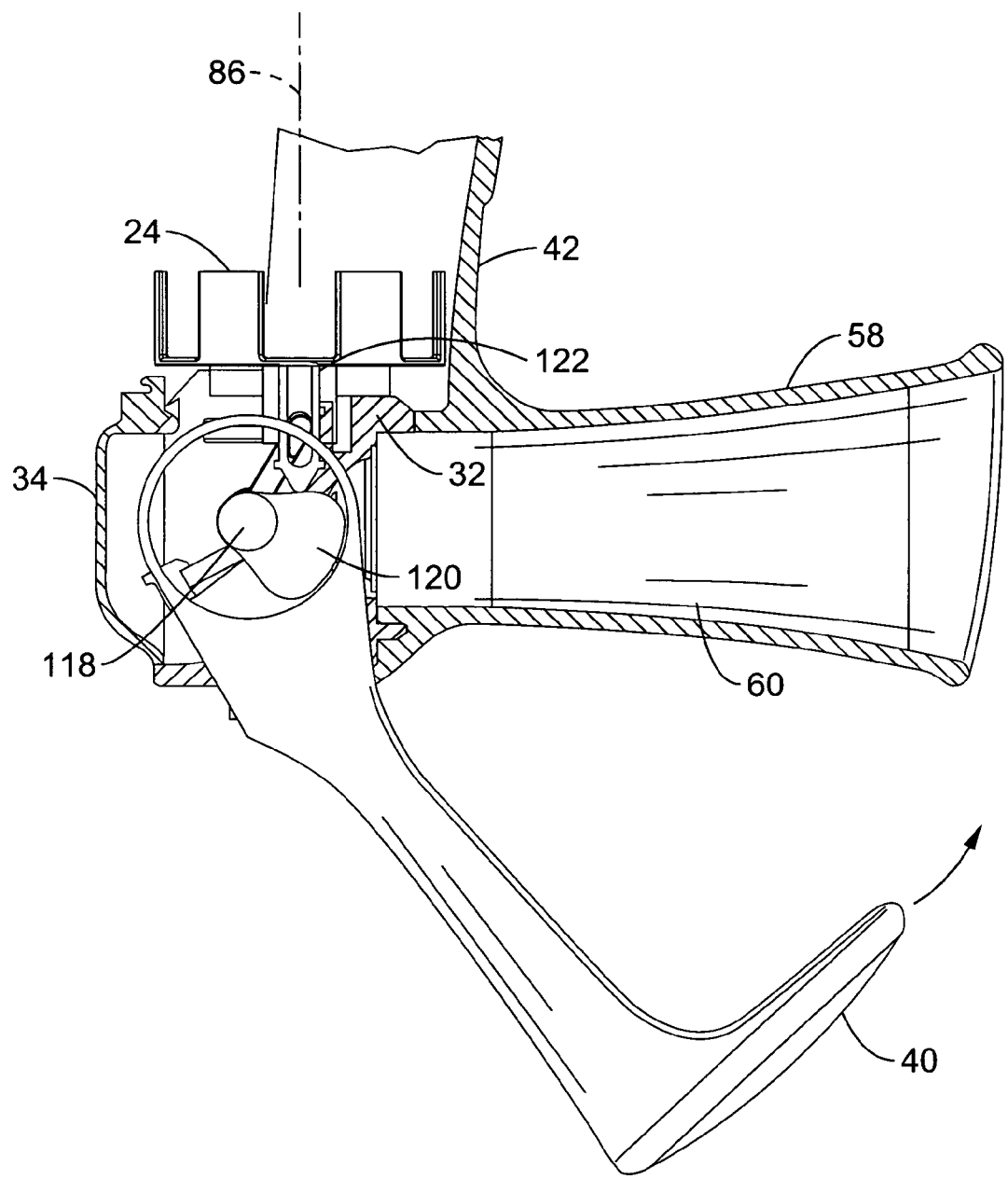

FIG. 7D illustrates the device of FIG. 7B with the cam of the dust cover driving the release mechanism back to the stowed configuration.

Figure 8A:
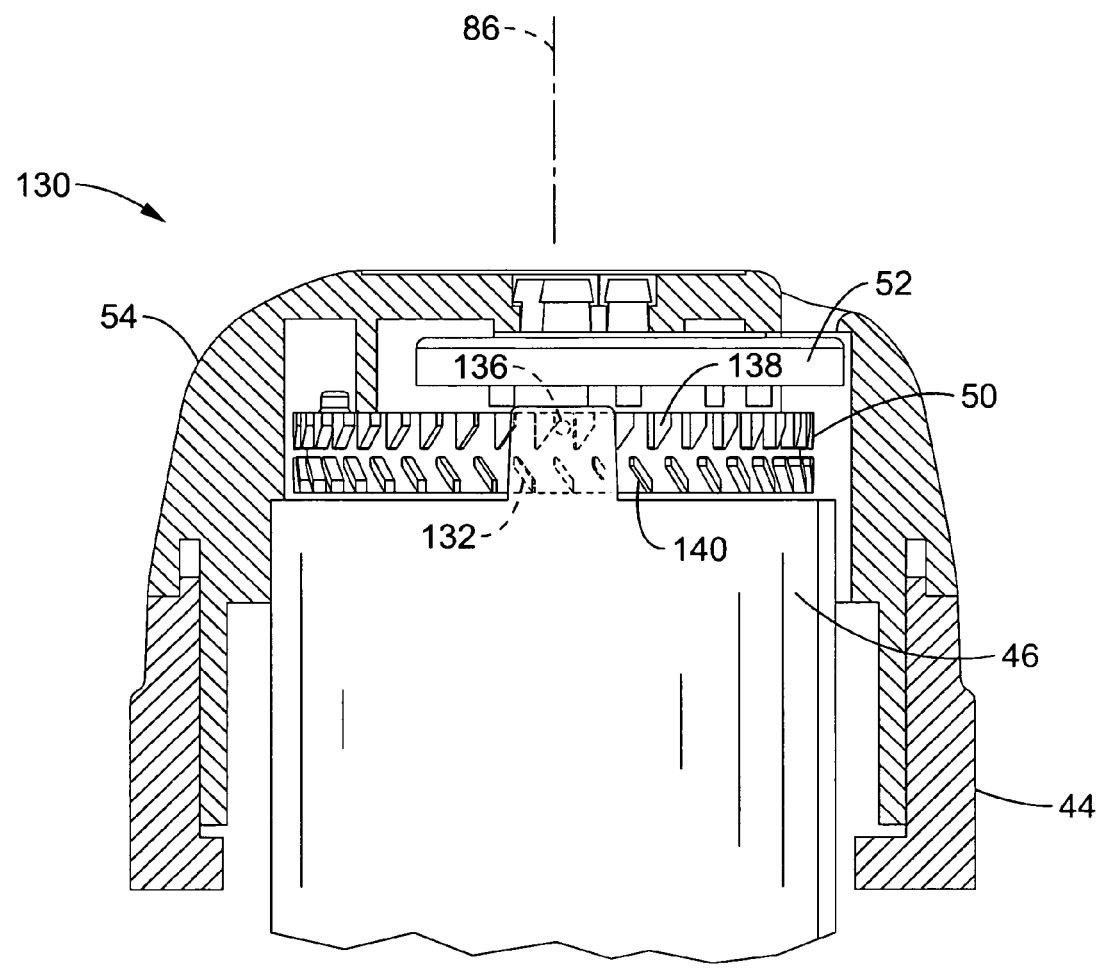

FIG. 8A is a cross-sectional view of the outer cover of the device to illustrate the dose counting mechanism of an embodiment of the present invention in a stowed configuration.

Figure 8B:
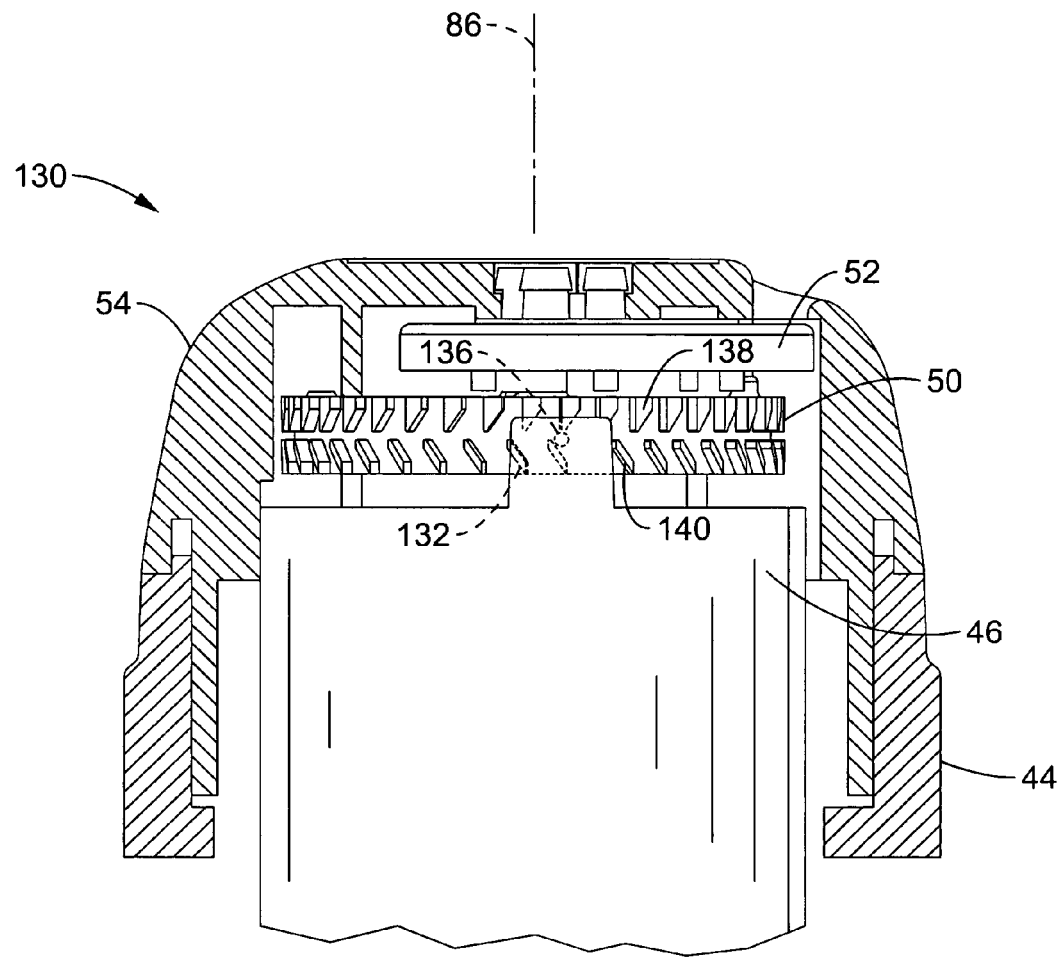

FIG. 8B illustrates the device of FIG. 8A with the container sleeve traveling part way through the discharge of the fluid source.

Figure 8C:
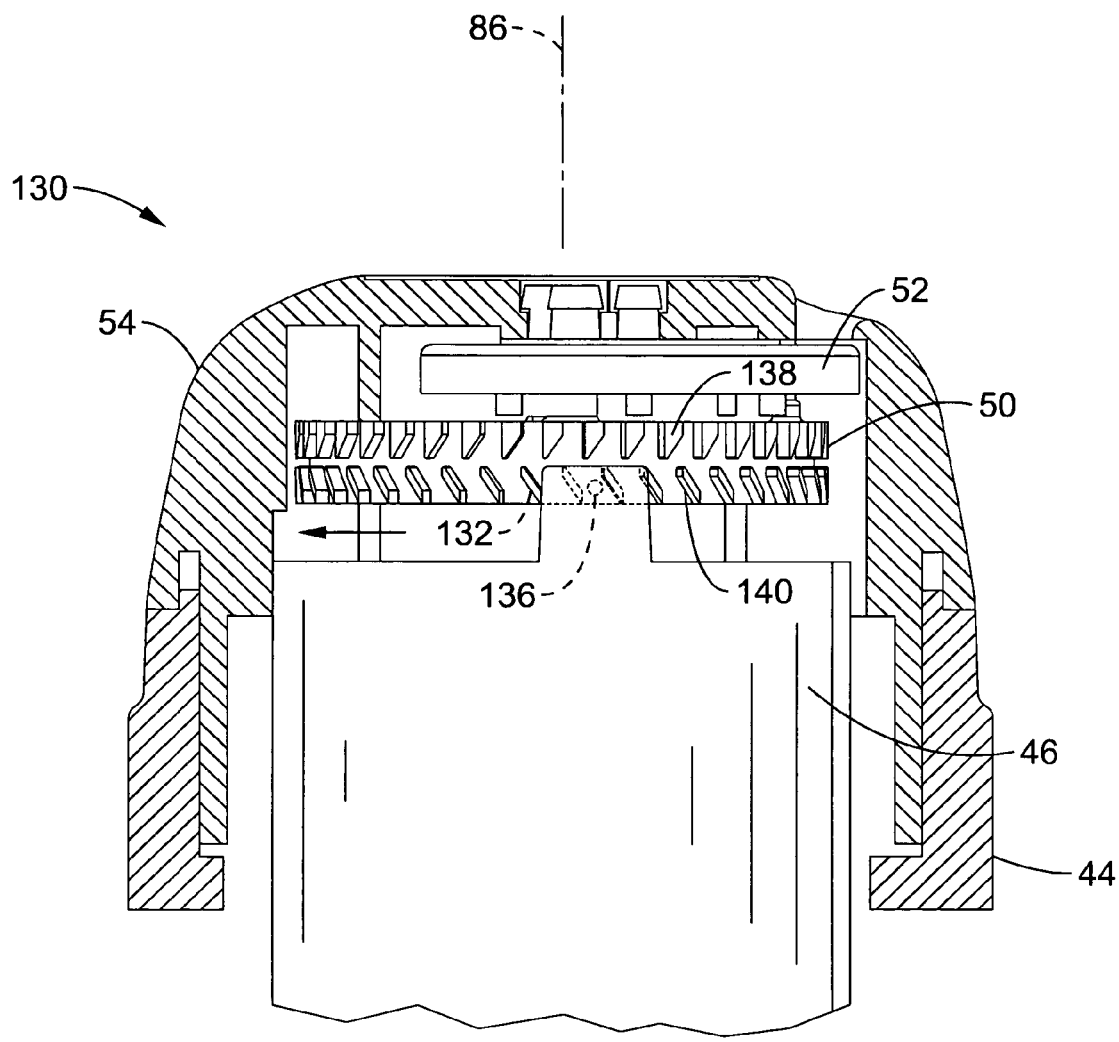

FIG. 8C illustrates the device of FIG. 8A with the container sleeve at the fully discharged configuration.

Figure 8D:
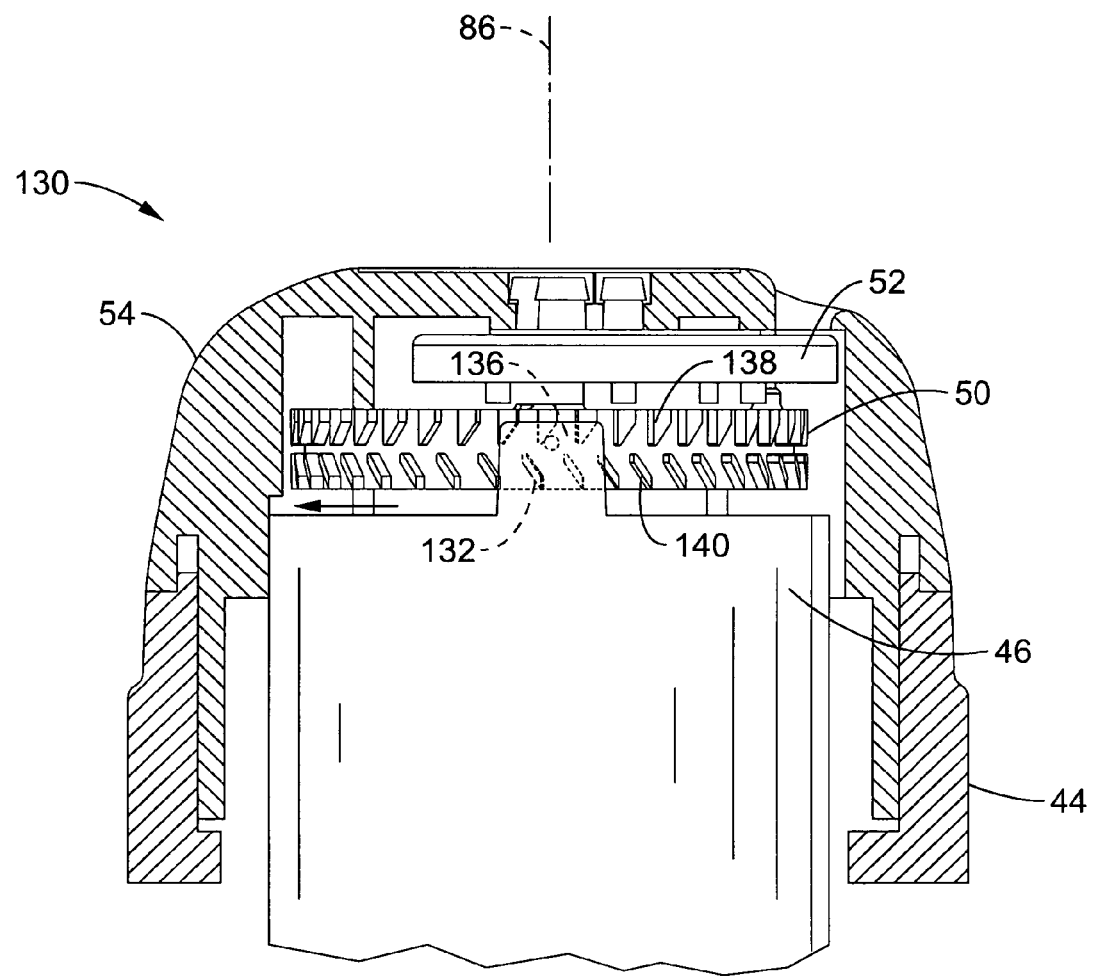

FIG. 8D illustrates the device of FIG. 8A with the container sleeve returning to the stowed position.

Figure 9:
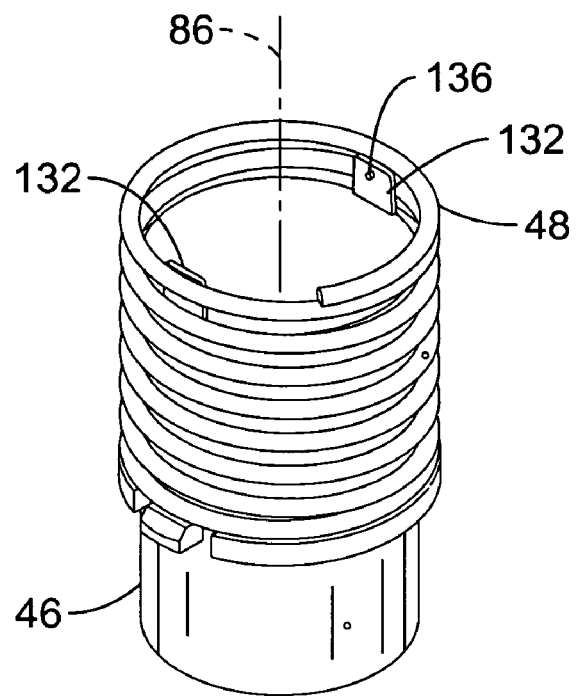

FIG. 9 is a schematic view of the container sleeve and biasing spring of the present invention.

Figure 10:
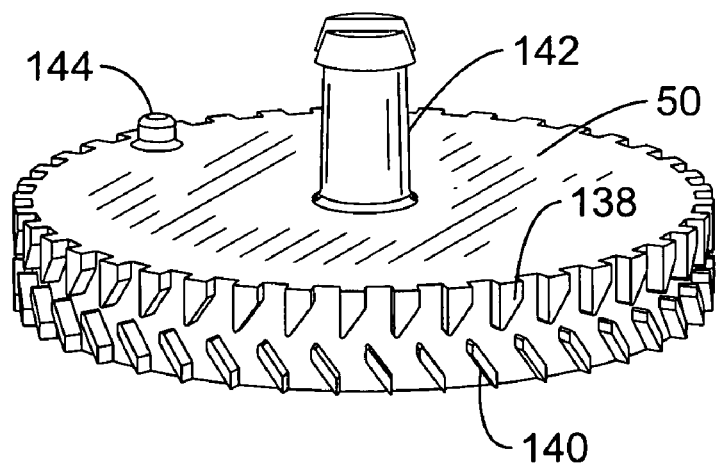

FIG. 10 illustrates an embodiment of the dose counter wheel of the present invention.

Figure 11A:
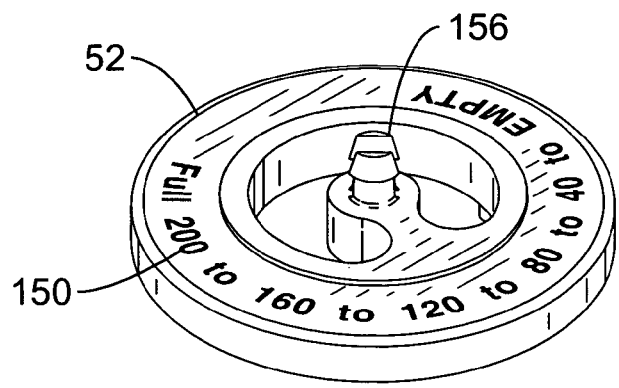
Figure 11B:
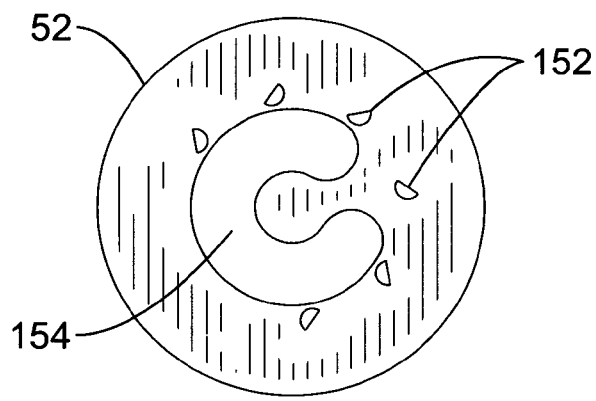
Figure 11C:
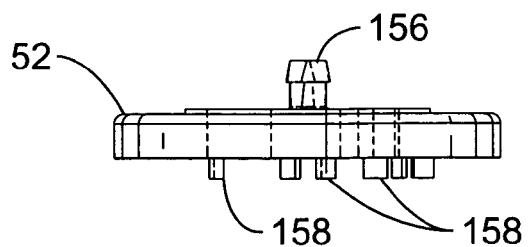

FIGS. 11A-C illustrate an embodiment of the display wheel of the present invention.

FIGS. 12A-E are schematic views of the dose counter wheel and display wheel through various counting configurations.

Figure 13:
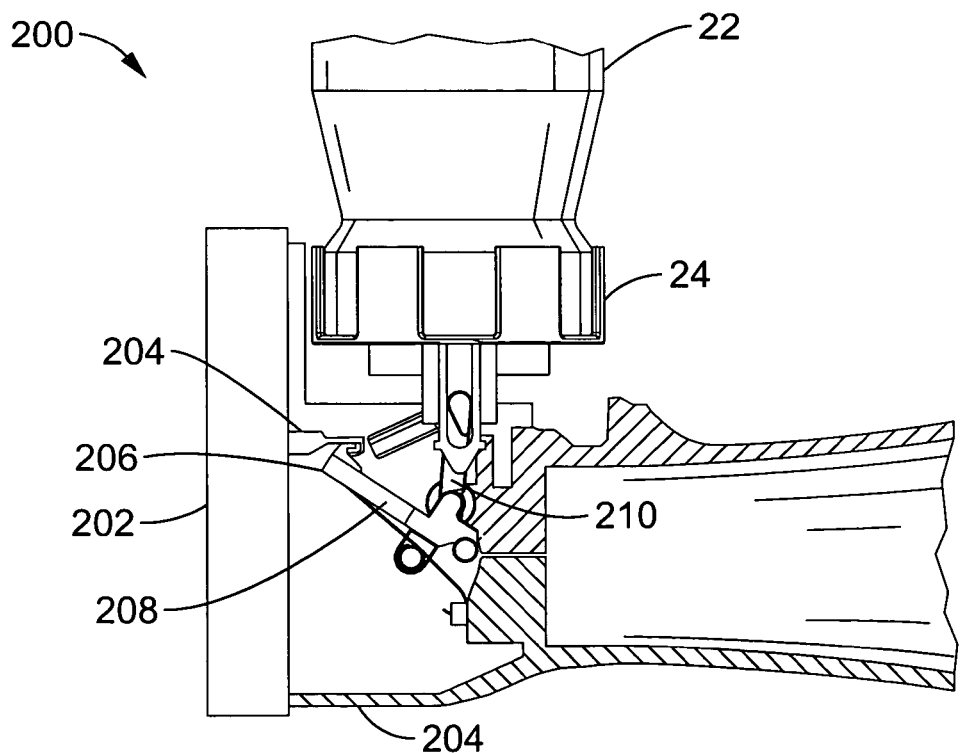

FIG. 13 is a cross-sectional view of an alternative embodiment of the present invention having a release mechanism using a diaphragm.

Figure 14:
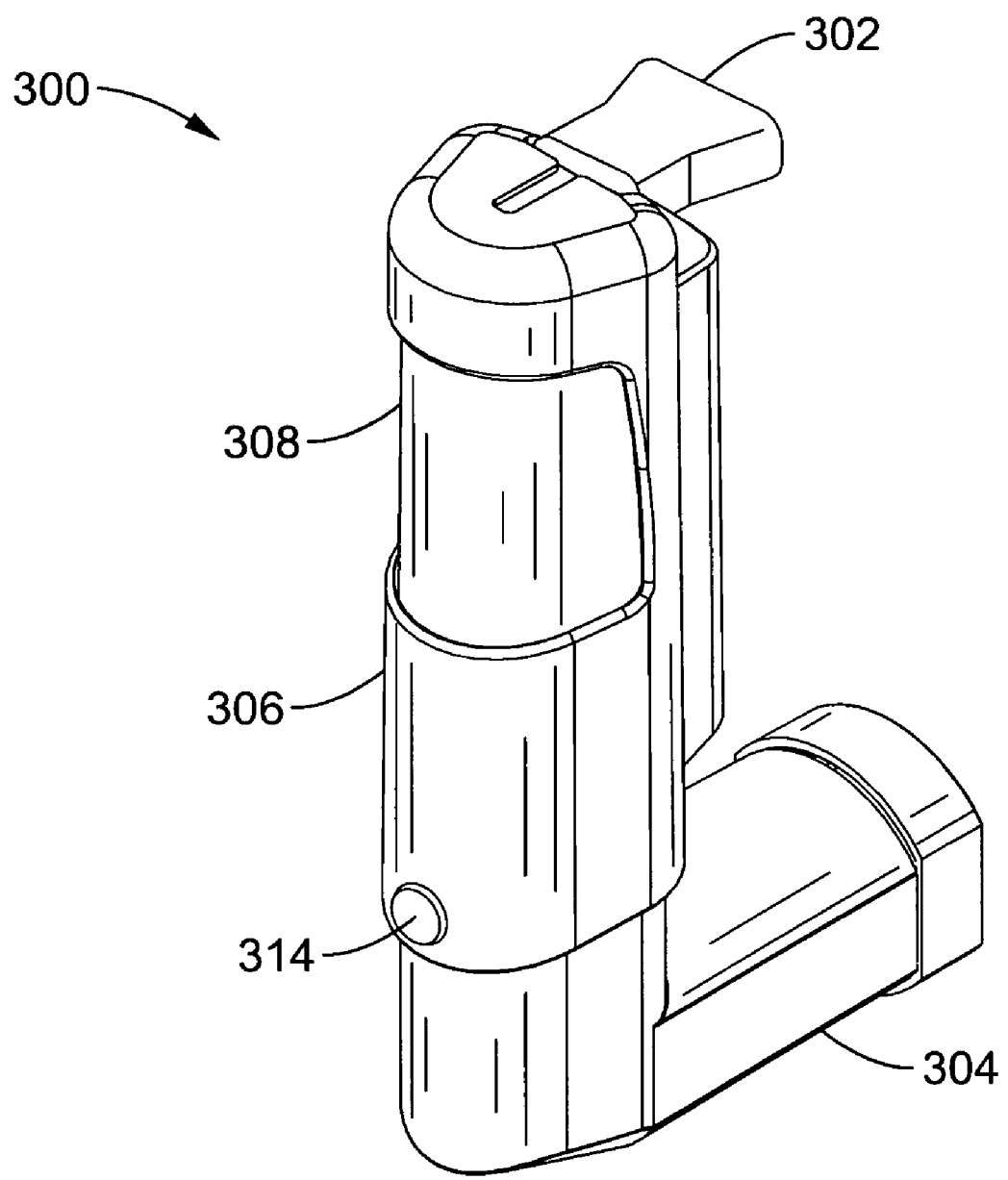

FIG. 14 is a perspective view of an alternative embodiment of the present invention having a release mechanism above the fluid source.

Figure 15:
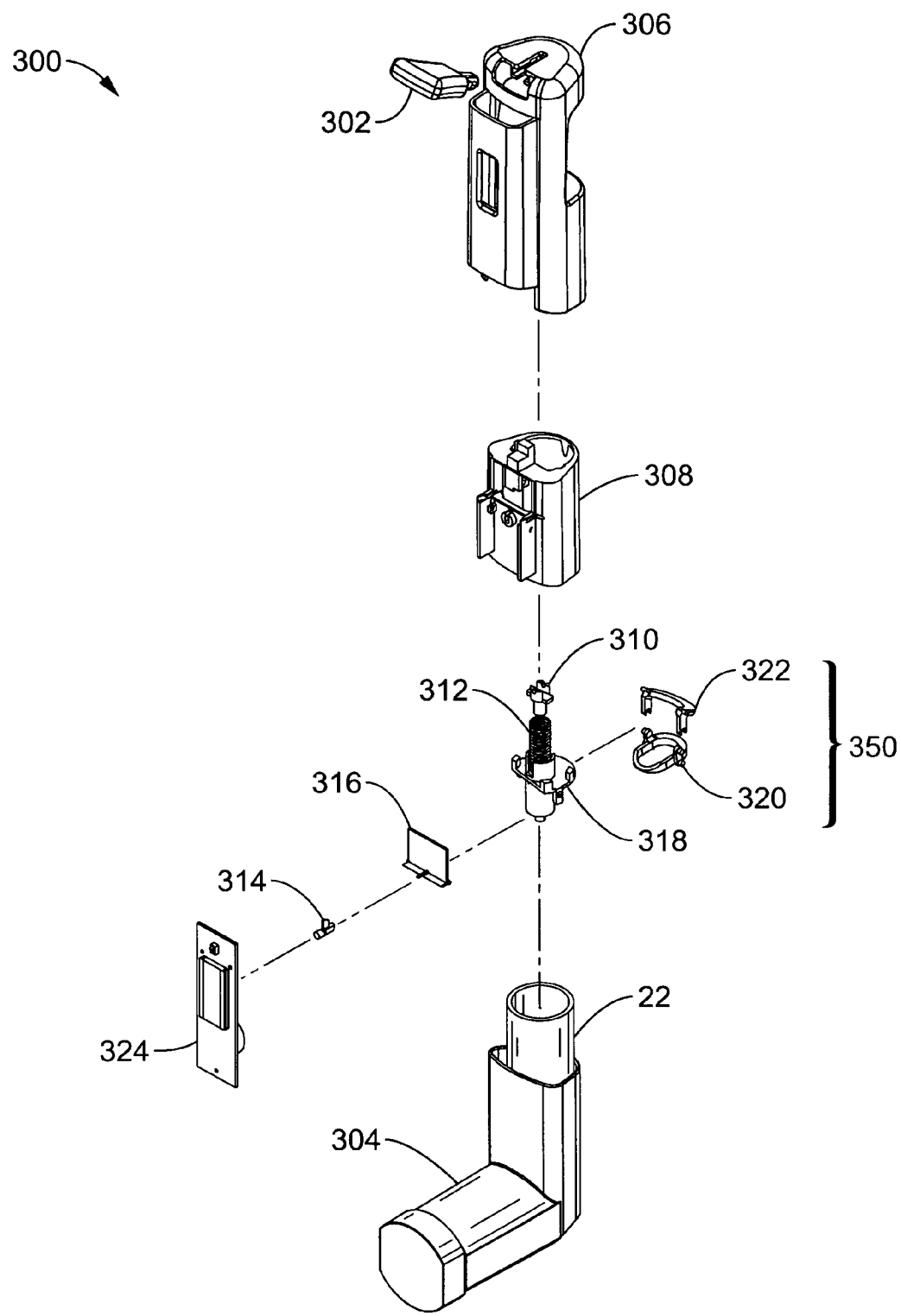

FIG. 15 is an exploded view of the device of FIG. 14.

FIGS. 16A-D are schematic views of the device of FIG. 14 traveling trough its range of motion from the stowed position, to discharge position, back to the stowed position.

Figure 17:
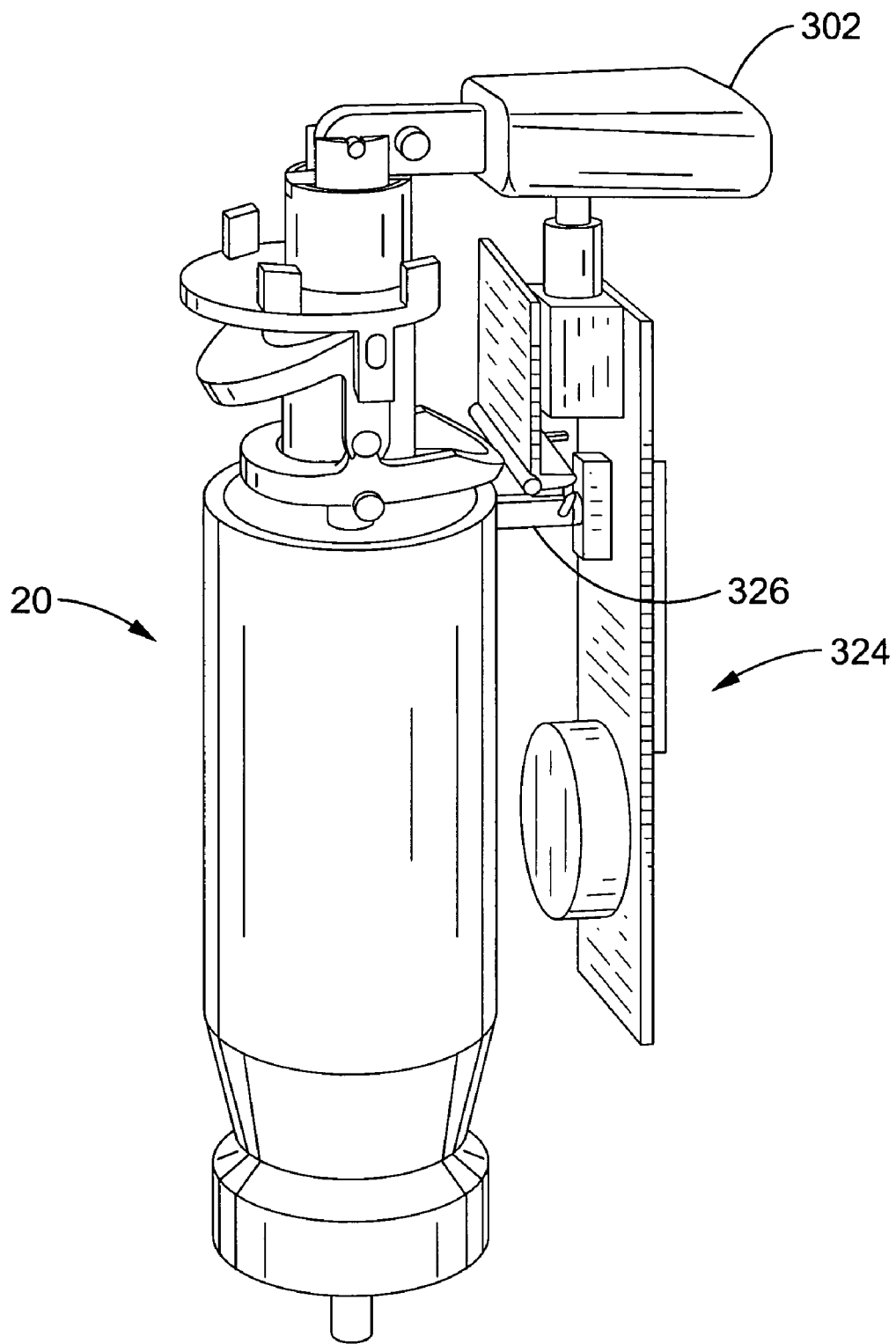

FIG. 17 illustrates the device of FIG. 14 having an electronic dose counter.

Figure 18:
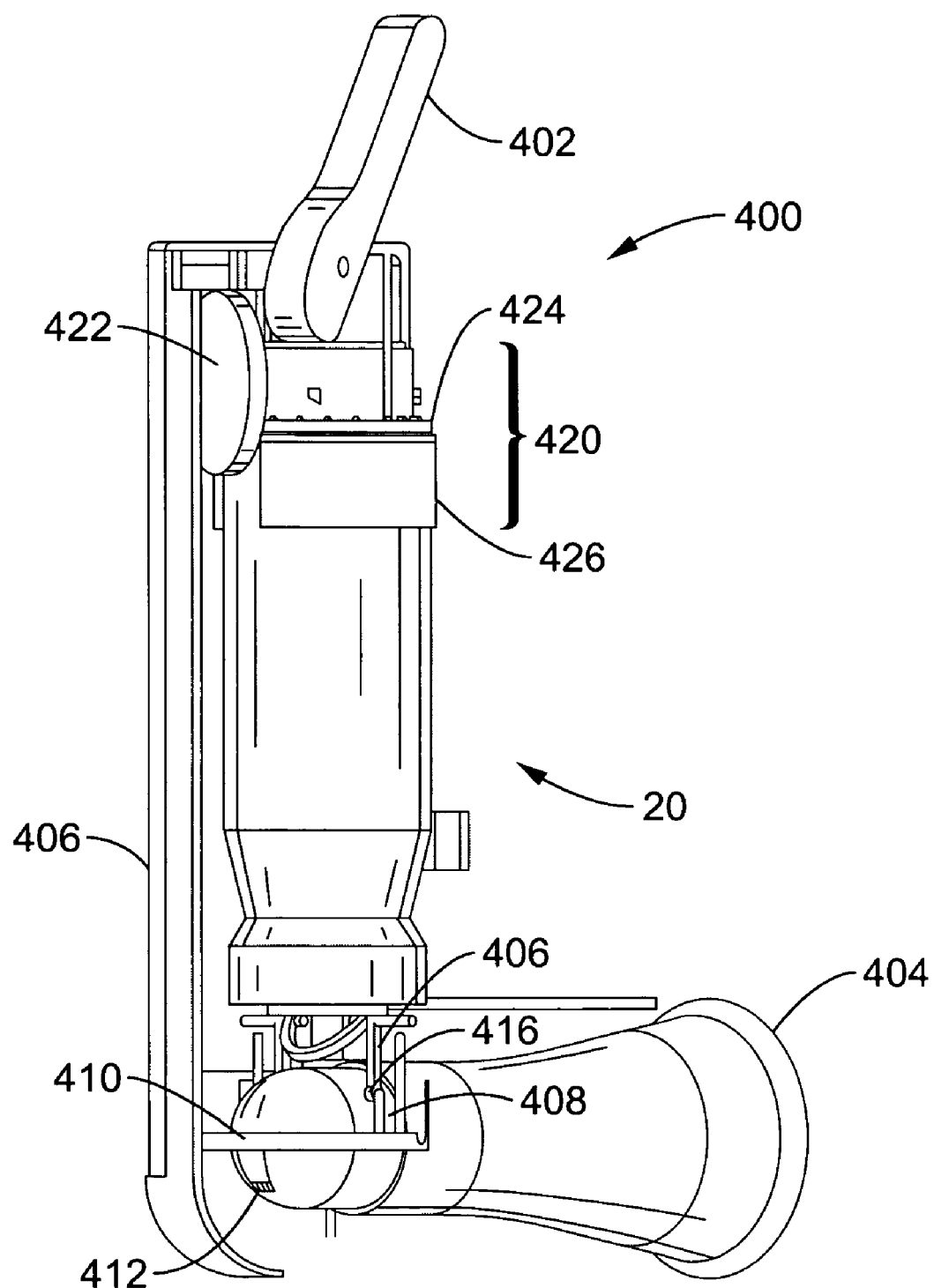

FIG. 18 is an alternative embodiment of the present invention with a portion of the outer cover removed to show the release mechanism and a mechanical dose counter with a vertically mounted display wheel.

Figure 19A:
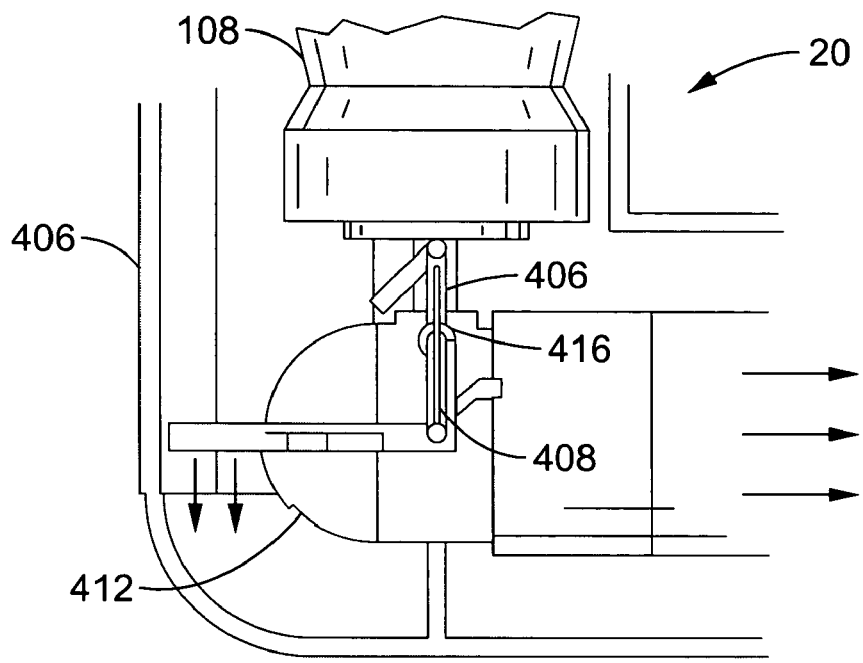
Figure 19B:
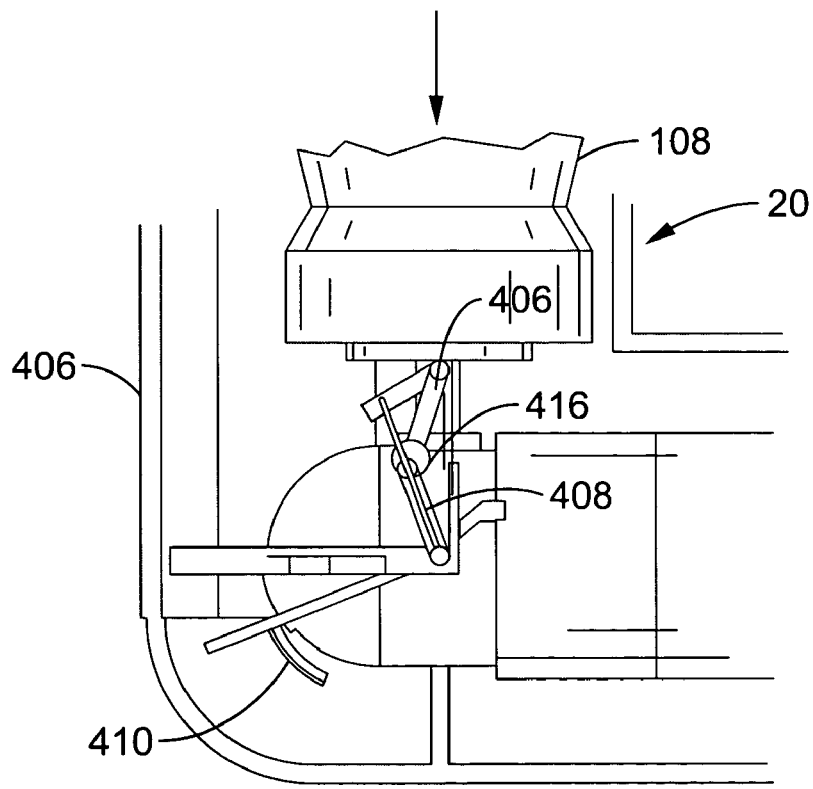

FIGS. 19A-B illustrate the release mechanism of the device of FIG. 18.

Figure 20A:
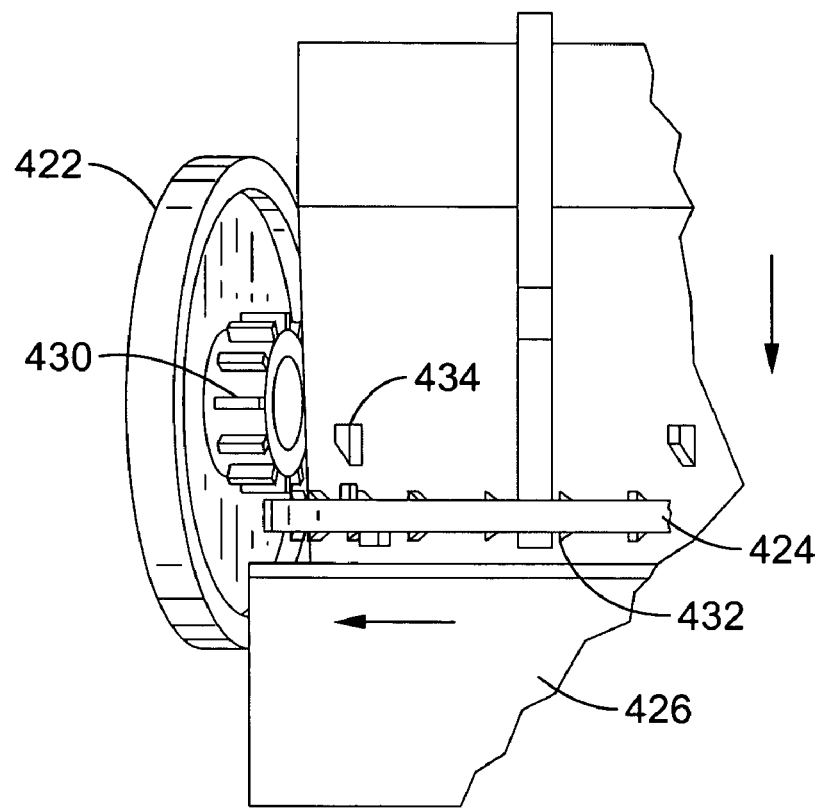
Figure 20B:
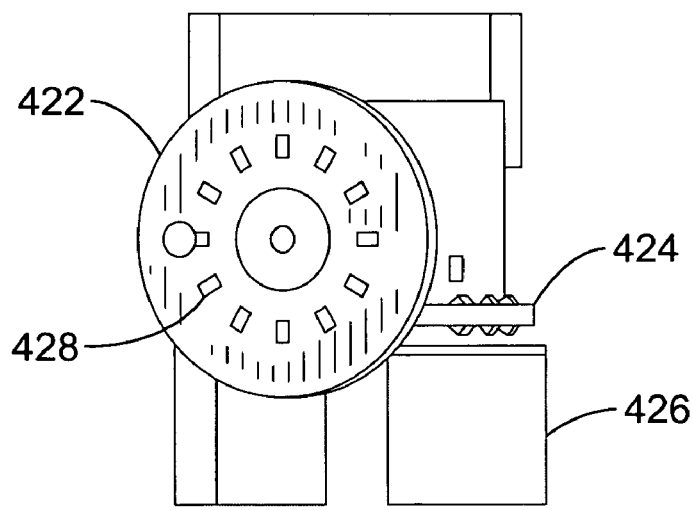

FIGS. 20A-B illustrate the dose counter of the device of FIG. 18.

DETAILED DESCRIPTION OF THE INVENTION

Referring more specifically to the drawings, for illustrative purposes the present invention is embodied in the apparatus generally shown in FIG. 1A through FIG. 20B. It will be appreciated that the apparatus may vary as to configuration and as to details of the parts, and that the method may vary as to the specific steps and sequence, without departing from the basic concepts as disclosed herein.

Figure 1A:
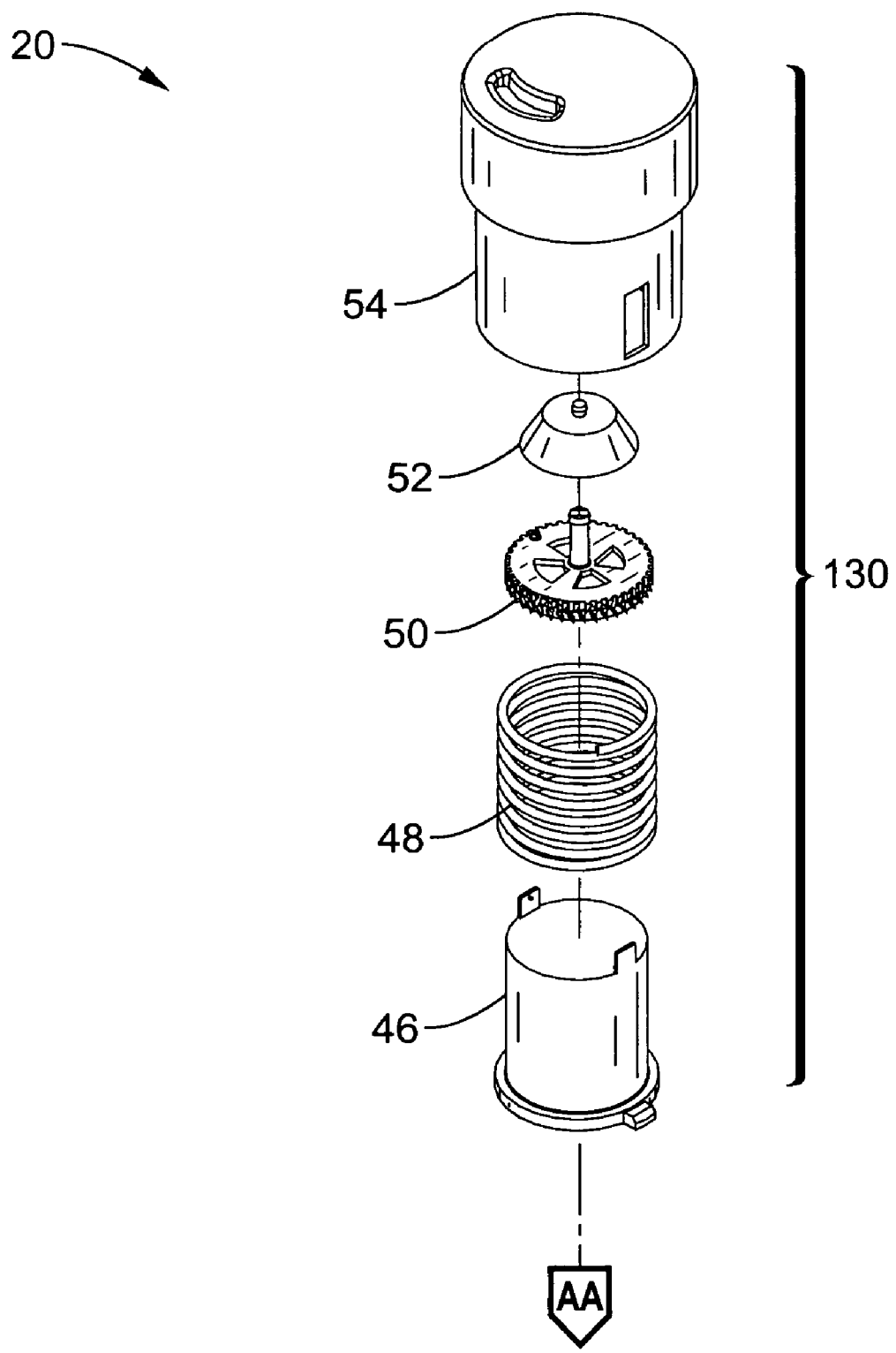
Figure 1B:
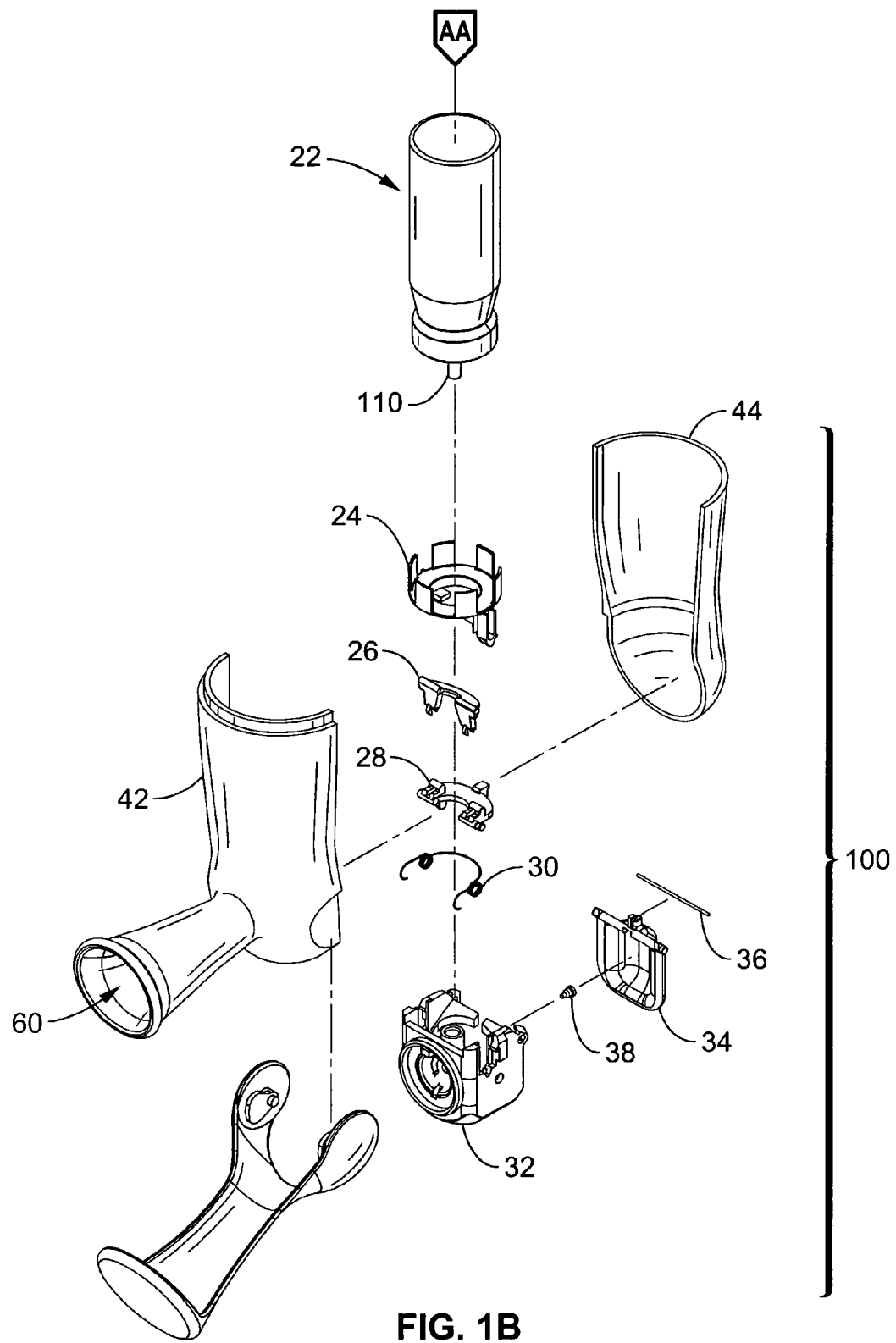

Referring first to FIGS. 1A and 1B, an inhaler 20 of the present invention is shown in an exploded view with a breath actuation assembly 100 and a dose counter assembly 130. The breath actuation assembly 100 and the dose counter assembly 130 are housed along with medicament fluid source 22 inside front cover 42, back cover 44, and top cap 54, all preferably comprising medical grade plastic or other suitable materials known in the art. Fluid source 22 may comprise a conventional Metered Dose Inhaler (MDI) container or other propellant based medicament readily available in the art. Fluid source 22 generally comprises container 108 holding a mixture of medicament and propellant, and nozzle 110, which is in line with the discharge axis 86 of the container 108, as shown in FIG. 6B. When the container 108 is advanced relative to the nozzle 110 in the direction of the discharge axis 86 (i.e. the nozzle 110 is pushed into the container 108), the medicament is discharged out the nozzle 110 in the direction of the discharge axis 86.

Turning now to FIGS. 2A through 2C, inhaler 20 is shown in an assembled configuration with dust cover 40 pivotally mounted to cover inhalation horn 58. The dust cover 40 may be rotated away from horn 58 to expose opening 60, as shown in FIG. 2B. A manual release button 62, as shown in FIG. 2C, may also be incorporated into the back cover 44. Top cap 54 has an opening 56 to give visual access to display wheel 52.

Referring also to FIGS. 1B and 3A through 3E, the breath actuation assembly 100 comprises a transducer 32 that rotatably houses lower link 28 at pivot 78. Lower link 28 is connected to upper link 26 at collapsible joint 66. Reference may also be made to FIGS. 5A-6B, wherein the transducer is illustrated in greater detail. Container holder 24 is shaped to receive the nozzle end of container 108 such that the nozzle 110 passes through to contact surface 112 of the transducer 32. Container holder 24 also has a pair of guides 122 having slots 90 sized to house a pair of bosses 92 as shown in FIG. 7A at the upper end of upper link 26.

As shown in FIGS. 3A through 4B, flap 34 is rotatably mounted to the transducer 32 via peg 98, which extends across the top surface of flap 34, and holes 114 in the sidewalls of transducer 32. The bottom and side extremities of flap 34 are sized to fit within the internal surface of transducer 32 to form gap 76. The flap 34 has an upper surface 72 configured to retain arm 74 of lower link 28 when the flap is in its nominal position shown in FIG. 3A.

As illustrated in FIGS. 6A and 6B, the transducer 32 is configured to receive nozzle 110 of fluid source 22 at surface 112. The transducer also comprises an inlet 106 that spans from surface 112 to a first chamber 102. The inlet 106 is configured to be in line with the nozzle 110 and discharge axis 86 such that medicament discharged from the fluid source 22 is received through the inlet 106 and downstream into first chamber 102.

The transducer 32 is also configured to receive plug 38 having bluff surface 104. Fluid entering chamber 102 through inlet 106 is dispersed and redirected by plug 38 and into outlet 124 that terminates downstream at section 68 of second chamber 64. The fluid dispersion characteristics of transducer 32 can be seen in greater detail with reference to U.S. Pat. No. 4,972,830 and EP308524B, which are expressly incorporated by reference herein.

The fluid source 22 is biased to discharge along axis 86 by compressing biasing spring 48 between the top cap 54 and container sleeve 46, which is adapted to receive the other end of the container 108 opposite the nozzle 110. Biasing spring 48 preloads the container 108 to move in the direction of surface 112 of transducer 32 along the discharge axis 86.

Figure 3A:
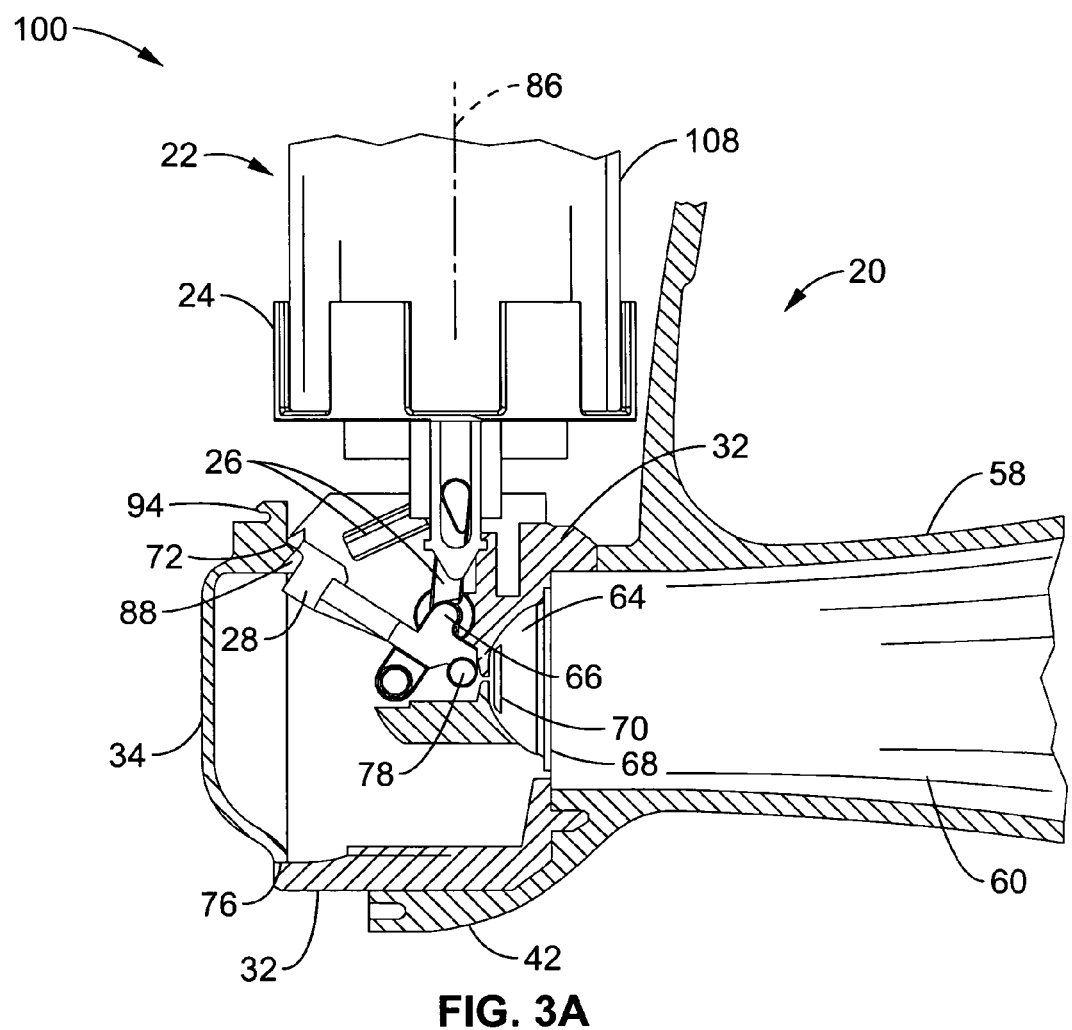
FIG. 3A is a cross-sectional view detailing the release mechanism of the present invention in a stowed configuration.

In the stowed configuration shown in FIG. 3A, the fluid source container 108 is retained from translating along axis 86 by a collapsible linkage comprising upper link 26 and lower link 28. Upper link 26 and lower link 28 are rotatably coupled at a collapsible knee-type joint 66. As illustrated in FIG. 3A, the downward force imposed by biasing spring 48 is restrained when joint 66 is held over-center by flap 34.

Figure 3B:
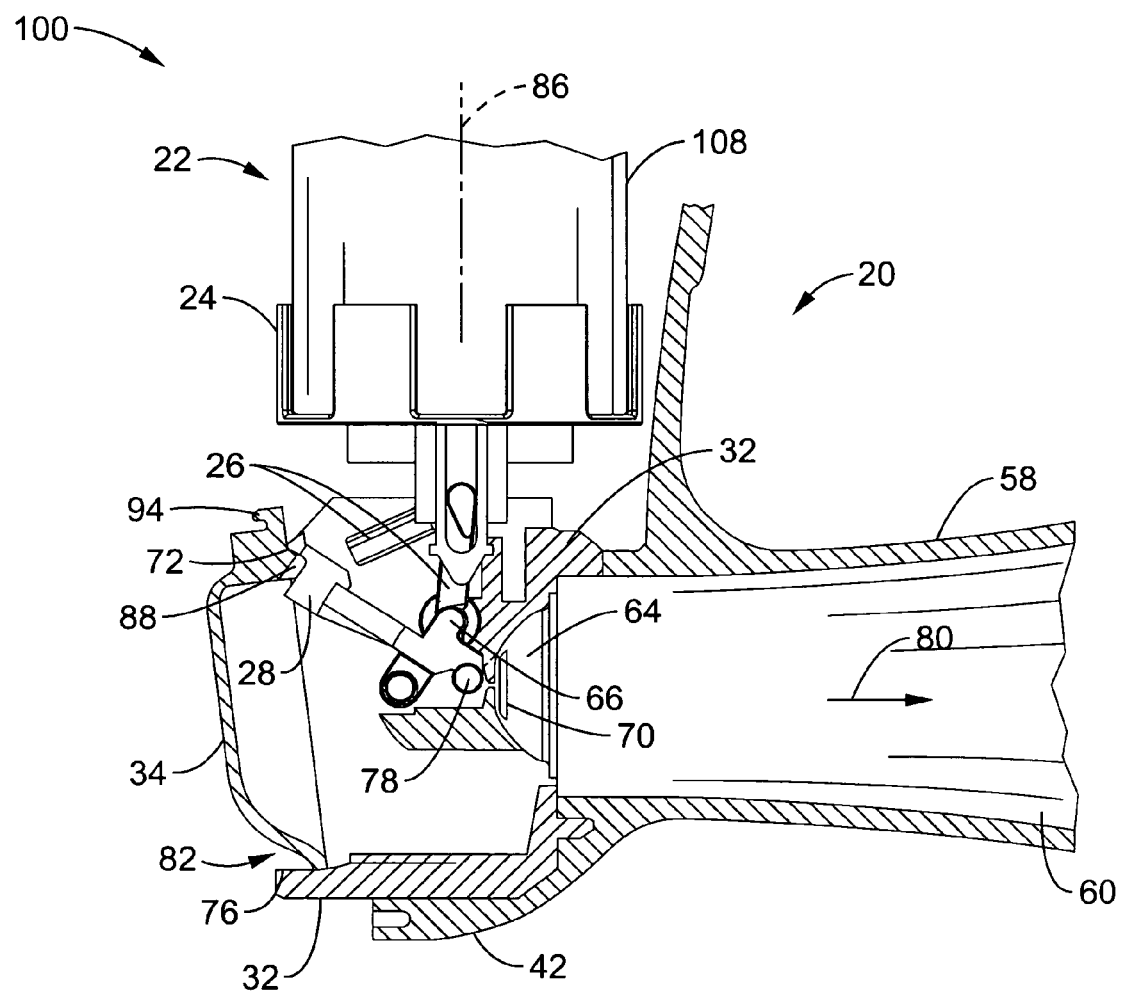
FIG. 3B illustrates the device of FIG. 3A with the flap rotated as a result of inhalation forces.
Figure 3C:
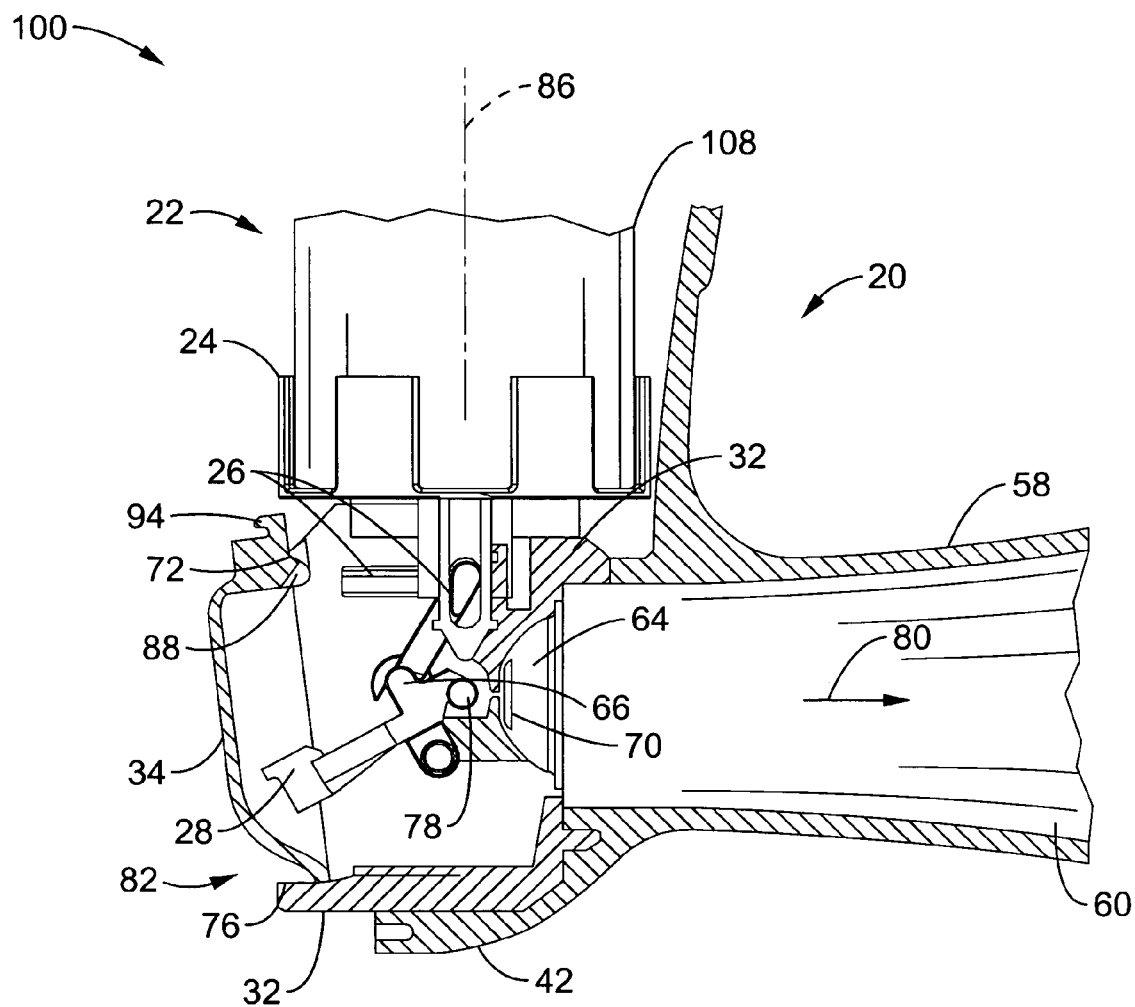
FIG. 3C illustrates the device of FIG. 3A with the collapsible knee in a collapsed configuration and the fluid source discharged.
Figure 4A:
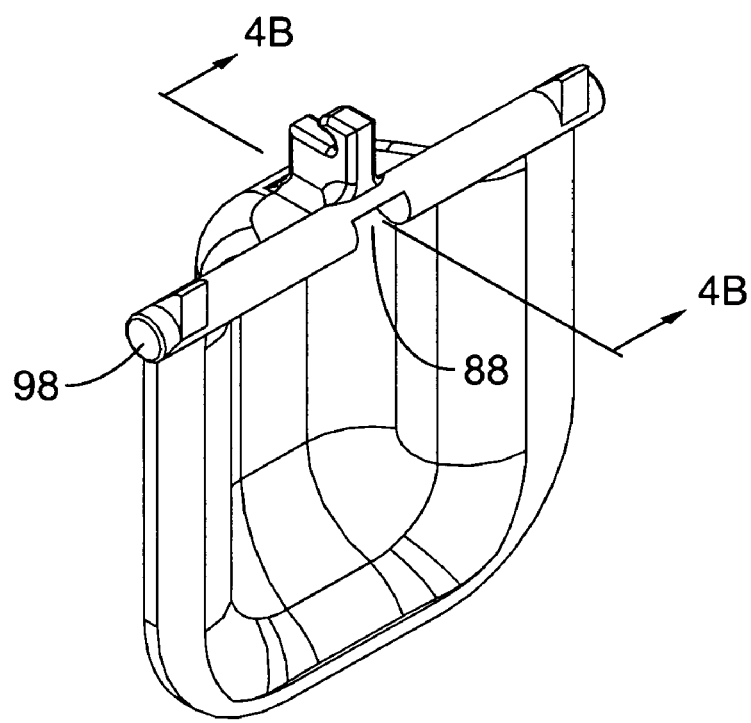
FIG. 4A is a perspective view of an embodiment of the flap of the present invention.
Figure 4B:
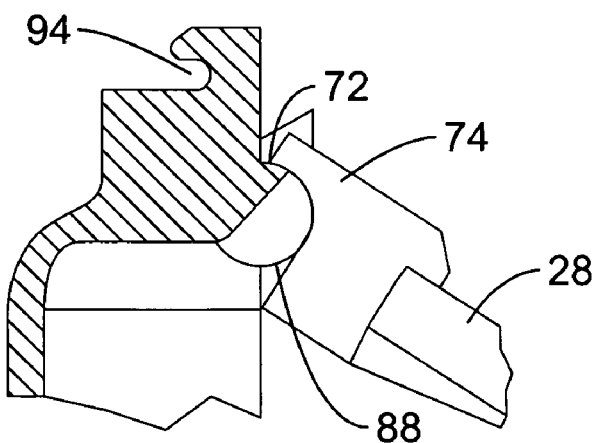
FIG. 4B illustrates a cross-sectional schematic view the flap of FIG. 3A with the lower linkage retained by the flap in the stored configuration.

FIG. 3B illustrates the initiation of the breath actuation mechanism 100 caused by inhalation by a patient through the opening 60 of horn 58. As shown in FIGS. 3B-3C and 4A, an outward airflow 80 is created in the second chamber 64, which pulls through a plurality of slots 70 in the transducer. Suction of air through slots 70 creates a small pressure differential 82 across the inner surface of flap 34, causing the flap to rotate about peg 98 and into the cavity of the transducer 32, as illustrated in FIGS. 3A and 3B. The gap 76 between the flap 34 and the transducer 32 provides enough clearance to allow the flap to rotate into the cavity of the transducer, while also being small enough to allow a pressure differential with minimal suction on the horn. As the flap 34 rotates, arm 74 of the lower link 28 is no longer retained by the upper surface 72 of the flap, and the arm 74 clears the flap 34 through recess 88 as the lower link 28 is allowed to rotate about pivot 78.

With rotation of the lower link 28 as shown in FIG. 3C, the collapsible joint 66 moves over center, allowing the container holder 24 and container 108 to translate downward along axis 86, forcing a portion of the nozzle 110 into the container 108 to stimulate discharge of the medicament from the container 108. The medicament travels through the first chamber 102 and into the second chamber 64 where it is entrained with air flowing through slots 70, as described in further detail in U.S. Pat. No. 4,972,830, previously incorporated by reference. In the embodiment shown, the second chamber 64 has an internal cross section that is shaped like a parabola. The entrained medicament flows through the second chamber 64 and out of the opening 60 of horn 58 to be inhaled by the patient. Therefore, the release of the metered dose of medicament is timed to be inhaled by the patient at an optimal moment during the inhalation phase of the patient's breath cycle.

Figure 3D:
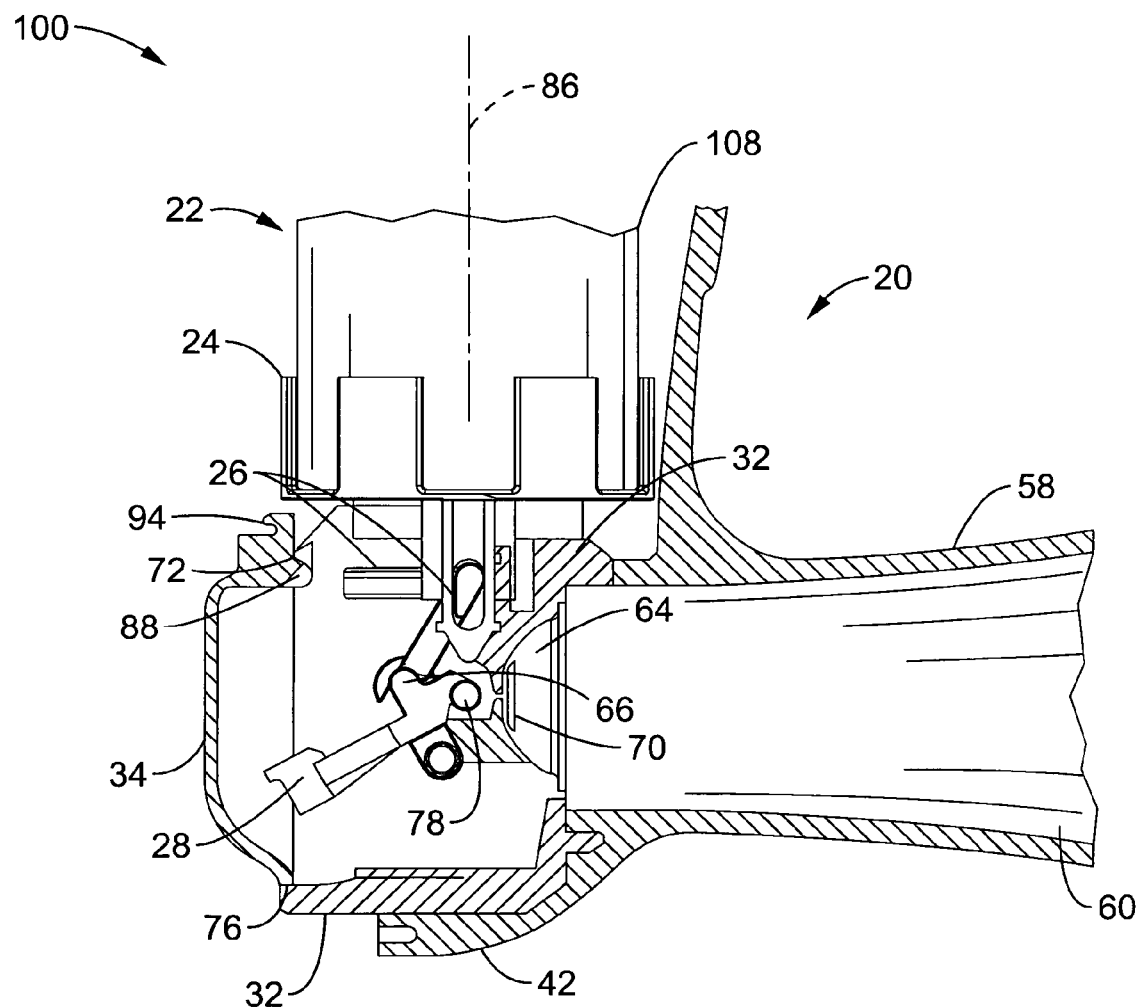
FIG. 3D illustrates the device of FIG. 3A with the flap returned to the stowed position and the collapsible knee still in a collapsed configuration.
Figure 3E:
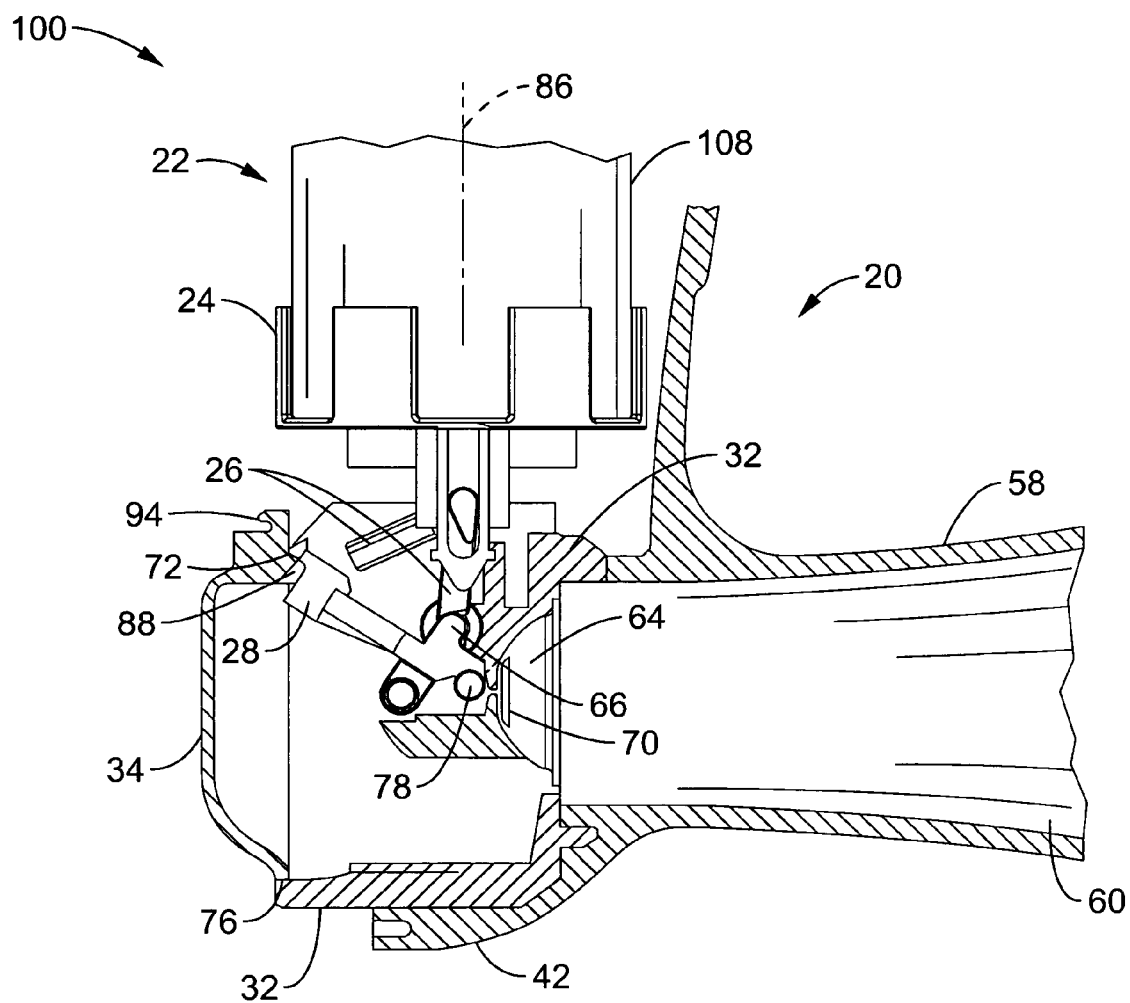
FIG. 3E illustrates the device of FIG. 3A with the release mechanism returned to its stowed configuration.

After the inhalation of the dose by the patient, the flap is returned to its nominal position shown in FIG. 3D by a return force exerted by flap spring 36. Flap spring 36 is a metallic rod or wire assembled between retention arms 96 of the transducer 32 and flange 94 on the flap 34. Rotation of the flap bends the spring to create a return force to return the flap 94 to its nominal position after the inhalation forces have subsided.

The upper and lower links 26, 28, container holder 24, and container 108 remain in the collapsed discharge position as seen in FIG. 3D due to the force imposed by the biasing spring 48. The return of the dust cover 40 (described in greater detail with reference to FIGS. 7A-7E below) to cover the horn 58 manually forces the container holder 24 and container 108 to return to the stowed position under compression from biasing spring 48. Return torsion spring 30 is mounted on lower link 28 to engage the transducer 32 such that a torsional force is exerted on the collapsible linkage to return to the locked configuration. The collapsible joint 66 is thus retained from collapsing once the dust cover 40 is again opened.

Turning to FIGS. 7A-7E, the operation of the dust cover 40 will now be described. In the present embodiment, the dust cover 40 not only serves as a shield to cover horn entrance 60, but it also serves to reset the container to the stowed position after discharge of the medicament. FIG. 7A illustrates inhaler 20 in a stowed configuration with the dust cover 40 shielding the entrance 60 to horn 58. The dust cover 40 is pivotably connected to the transducer 32 such that it can be rotated out of place to allow access to the horn opening 60. In alternative embodiments, the dust cover may be pivotably connected to either the front or back covers 42, 44. The dust cover 40 has two cams 120, which are configured to engage the bottom surface of guides 122 of container holder 24 through its entire range of motion along axis 86. When the dust cover 40 is rotated about pivot 118 (shown in FIG. 7B), the cams disengage guides 122. The container holder 24 and container 108 remain in the stowed position from the over-center orientation of the collapsible linkage.

FIG. 7C illustrates the breath actuation assembly 100 in the collapsed configuration with the container holder 24 and container 108 in the discharge position. The breath actuation assembly 100 is biased to remain in this configuration due to the compressive force of the biasing spring 48. When the dust cover is rotated back toward the horn opening 60, as shown in FIG. 7D, the cams 120 engage the bottom surface of guide 122, pushing the container holder 24 and container 108 upward along axis 86. When the dust cover 40 is in its final stowed position covering the horn entrance 60, the cams 120 have pushed the container holder 24 to the stowed position, as shown in FIG. 7A. In this configuration, the return spring 30 has reset the breath actuation assembly 100 to the locked position, and movement of the container 108 will be retained by the collapsible linkage independent of the dust cover cams.

The inhaler 20 preferably includes a dose counter for automatically counting the remaining doses left in the container after each discharge of the medicament. The inhaler may be configured with a dose counter having a number of different configurations, including mechanical or electrical counters. The operation of a preferred embodiment utilizing a mechanical dose counter assembly 130 will be described with respect to FIGS. 8A to 12E.

FIG. 8A illustrates inhaler 20 with dose counter assembly 130 configured above the container sleeve 46. The container sleeve 46 is sized to receive the non-dispensing end of the container 108. The container sleeve preferably has one or more tabs 132 having a boss 136 configured to engage the teeth of first wheel 50 disposed just above the container sleeve 46. The embodiment shown in FIG. 9 has two tabs 132 and bosses 136. However, it will be appreciated that any number of tabs and bosses may be employed.

Referring back to FIG. 8A, first wheel 50 is a gear rotatably mounted in a horizontal orientation to top cap 54. Wheel 50 has a plurality of lower teeth 140 and upper teeth 138 disposed along the outer perimeter of wheel 50.

In a preferred embodiment, display wheel 52 is also rotatably mounted to top cap 54 in a horizontal orientation between first wheel 50 and the top cap. Display wheel 52 has an opening 154 to allow clearance for column 142 of first wheel 50 that is vertically disposed to mount to top cap 54. Display wheel 52 has markings 150 to indicate the number of doses left in the container 108 based on the position of the display wheel 52. As seen in FIGS. 2A and 2B, the markings 150 that are showing through opening 56 in top cap 54 indicate the number of remaining doses.

FIGS. 8A-8D illustrate the interaction between the container sleeve 46 and the first wheel 50 upon discharge of the fluid source 22. When the container 108 is in the stowed position, boss 136 lines up on the perimeter of wheel 50 between two of the upper teeth 138. As the container 108 and container sleeve 46 moves downward along the discharge axis as a result of the breath actuation mechanism, boss 136 contacts the upper incline of one of the lower teeth 140, as shown in FIG. 8B. The boss 136 continues its translation along axis 86, forcing the first wheel 50 to turn clockwise (looking down from the top) until the container 108 reaches the discharge position, as shown in FIG. 8C. When the dust cover 40 is closed to return the container 108 to the stowed position, boss 136 translates upward until contacting the lower incline of upper tooth 138, as shown in FIG. 8D. The boss 136 continues its upward translation, forcing the wheel 50 to further turn clockwise until the container 108 reaches the stowed position, shown in FIG. 8A. When another dose is dispensed, the cycle repeats.

The lower wheel 50 may be configured to vary the number of doses required to turn the lower wheel 360 degrees by varying the number of teeth. In the above embodiment, a 40-tooth index was used. However, this number may be varied depending on the number of doses included in the container.

Figure 12A:
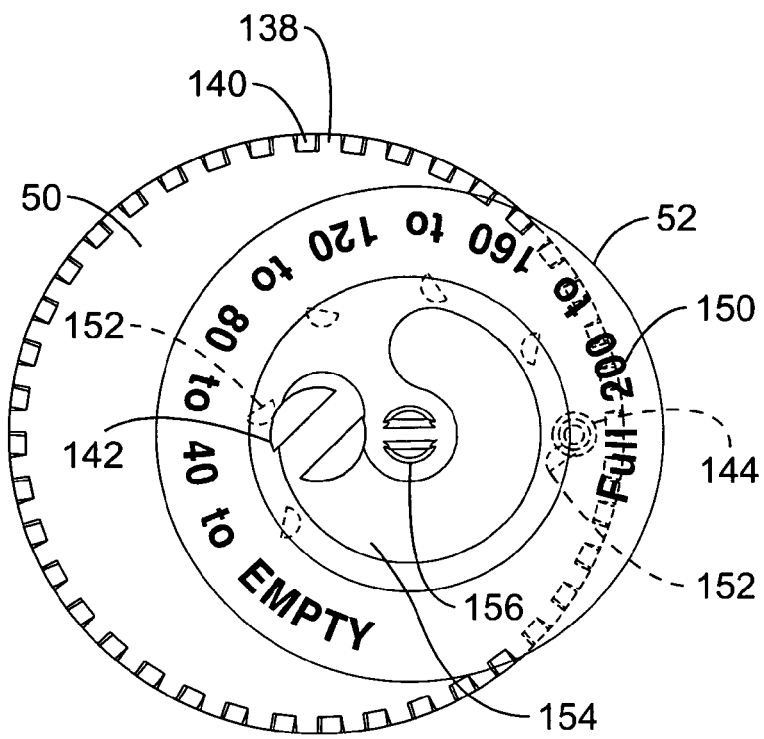
Figure 12B:
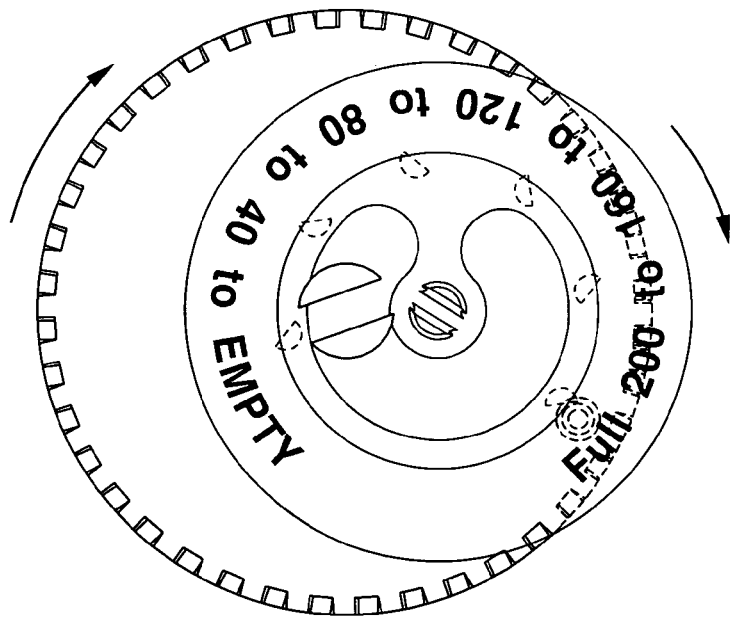
Figure 12C:
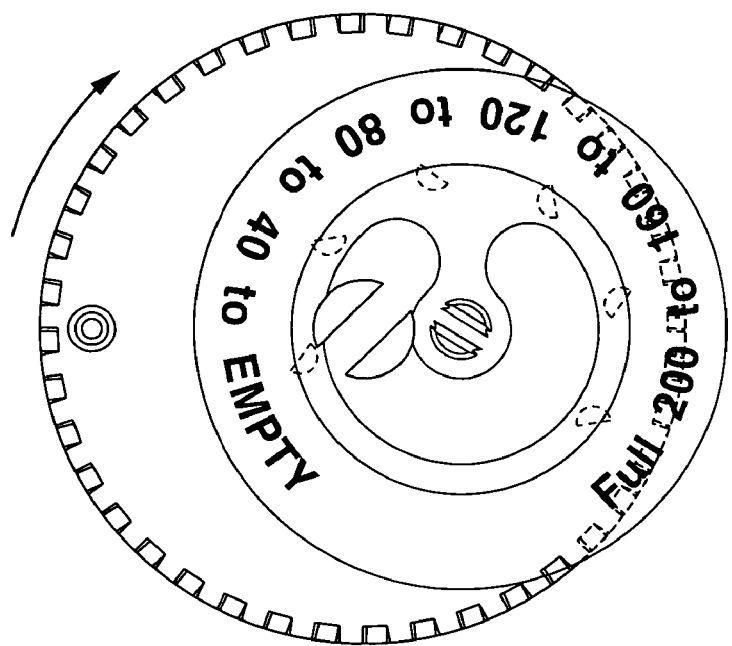
Figure 12D:
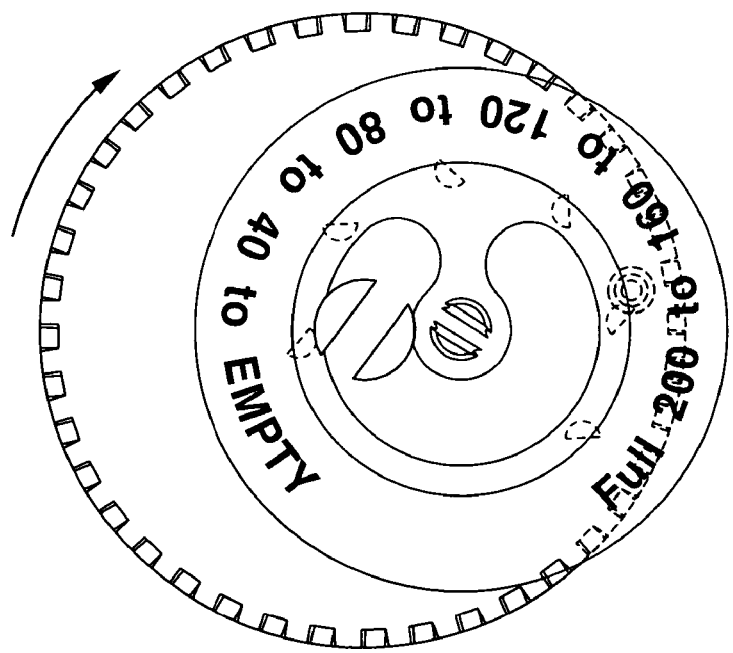
Figure 12E:
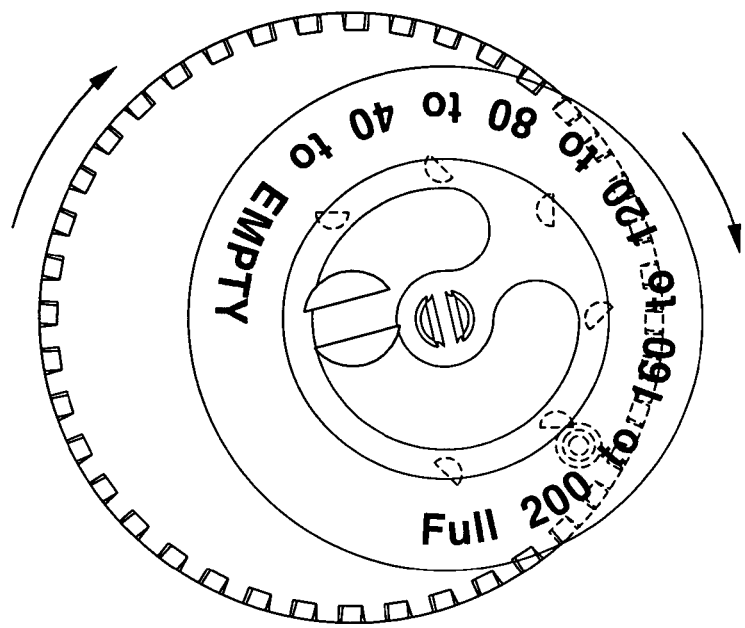

FIGS. 12A-12C illustrate the interaction between the display wheel 52 and the lower wheel 50. As shown in FIG. 10 and in hidden line in FIGS. 12A-12C, the lower wheel 50 has a drive peg 144 disposed on the upper surface of the lower wheel. Display wheel 52 has a plurality of semi-circular receiving pegs 152 disposed on the lower surface of the display wheel. As first wheel rotates about column mount 142, drive peg 144 engages a first of the receiving pegs 152 and causes the display wheel 52 to rotate about mount 156 a specified distance along mark 150, the specified distance indicating the range of doses left (e.g. "full 200 to 160") (see FIG. 12A). At a portion of first wheel's rotation, the drive peg 144 slips past the first of the receiving pegs 152 (see FIG. 12B) and continues to complete one full rotation (40 doses) until contacting the second of the receiving pegs 152 (FIG. 12C). The cycle repeats itself until all the receiving pegs 152 are driven such that the "empty" indicator is displayed at window 56 when the specified number of doses has been dispensed.

The effect of the gearing as shown in FIGS. 12A-C is to scale the motion of the display wheel 52 with respect to the first wheel 50. To change the scale of the motion, one or more additional driving pegs 144 may be disposed on the upper surface of the first wheel 50. For example, a second driving peg (not shown) may be disposed 180 degrees from the first such that the display wheel would advances twice as fast relative to the first wheel for a container having 100 total doses.

FIG. 13 illustrates an alternative embodiment showing an inhaler having a breath actuated release mechanism 200 using a diaphragm 202 rather than the flap 34 shown in FIGS. 1-7E. The diaphragm 202 is configured to mount to transducer 204 and be sized so that a portion of the diaphragm deflects in response to inhalation forces from the patient. Release mechanism 200 further includes a catch 204 coupled to the diaphragm and the lower link 208 to retain the collapsible linkage comprised of the lower link 208 and the upper link 210.

During use, inhalation forces from the patient deflect the portion of the diaphragm in communication with catch 204. Motion of the catch 204 allows lower link 208 to rotate past the catch, thereby allowing the 208/210 linkage to collapse and discharge fluid source 22.

FIGS. 14-17 illustrate another alternative embodiment of inhaler 300 having a load lever 302 and a breath actuated release mechanism 350 on top of fluid source 22. By placing the release mechanism above the MDI container, the mechanism can be applied to any MDI actuator with minimal mold modification. Inhaler 300 has a lower portion 304 housing fluid source 22 and a transducer (not shown) for dispersing the medicament. Middle body 308 interfaces with lower portion 304 and slideably houses plunger 318 to selectively advance fluid source 22 downward to discharge the medicament.

Figure 16A:
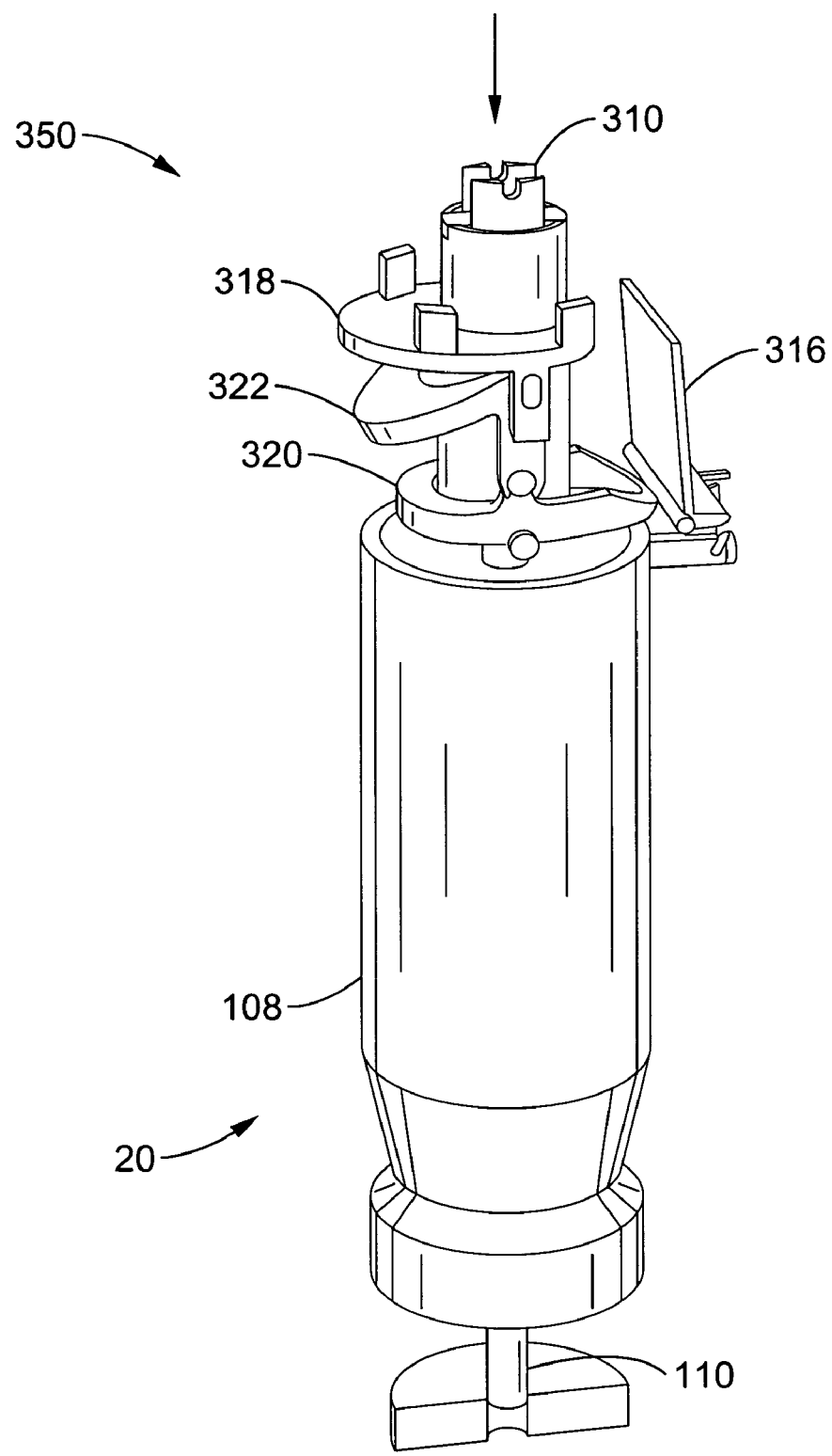

Plunger 318 is retained from moving relative to middle body 308 by a collapsible linkage comprising lower link 320 and upper link 322. Plunger 308 is also configured to receive biasing spring 312 at its up extremity. The biasing spring 312 is shaped to receive spring cap 310 which may be depressed to compress spring 312 against plunger 318 in a downward discharge direction, as shown in FIG. 16A. To depress spring cap 310, load lever 302 is rotatably attached to top shell 306 such that rotation of load lever 302 to a vertical orientation forces the spring cap 310 down to bias the plunger to discharge fluid source 22.

Figure 16B:
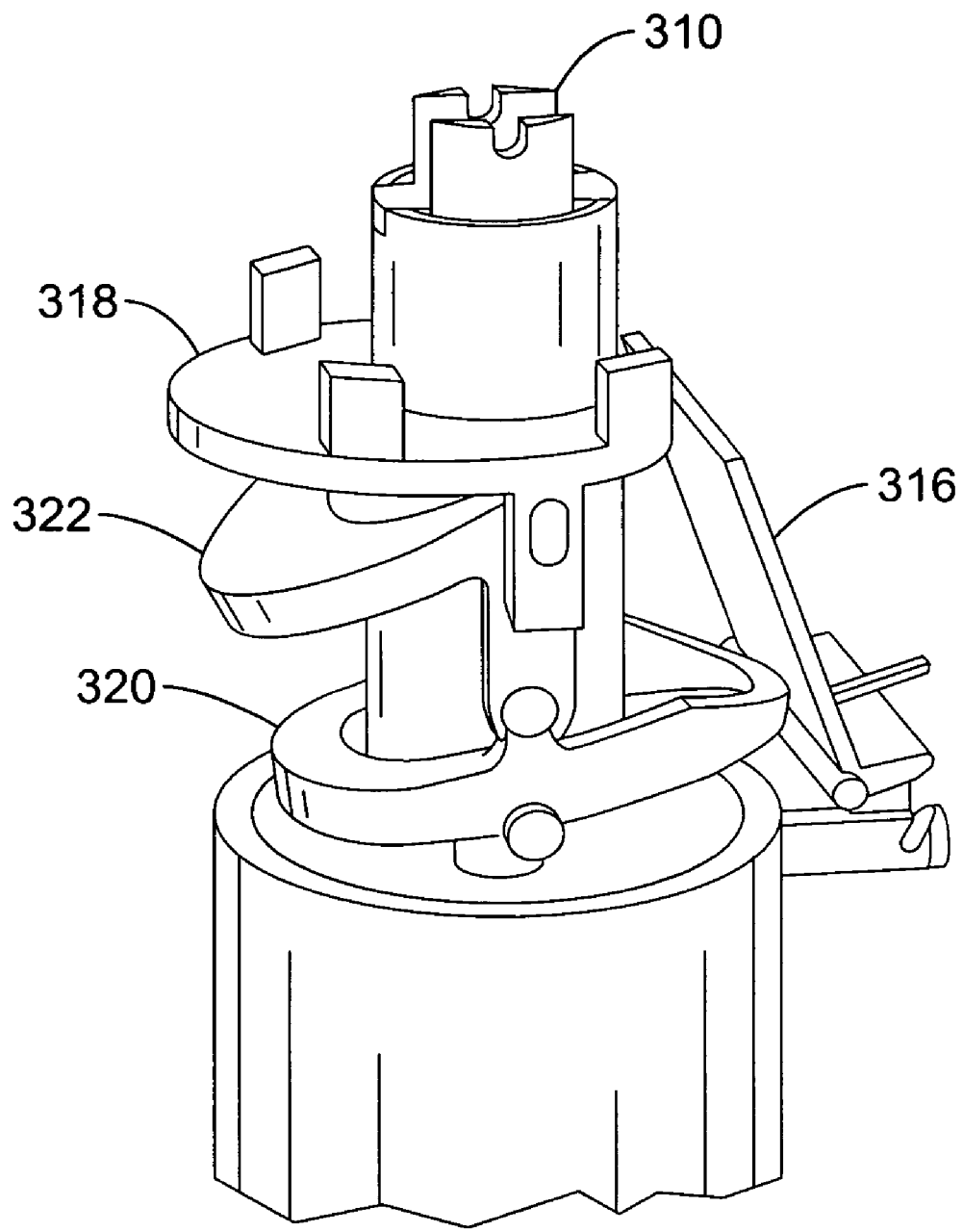

Motion of the collapsible link 320, and linkage 320/322, is restrained by flap 316. Flap 16 is pivotably mounted such that inhalation forces cause it to rotate as illustrated in FIG. 16B, thereby allowing the lower link 320 to rotate downward such that linkage 320/322 collapses. The biasing force from spring 312 forces the plunger downward as illustrated in FIG. 16C. The load lever 302 is then reset to the first position, allowing the fluid source 22 to translate back to the stowed position illustrated in FIG. 16D.

FIG. 17 illustrates an embodiment of the inhaler 300 incorporating an electronic dose counter 324. In such a configuration, flap 316 is coupled to trigger 326, which depresses a sensor in dose counter 324 each time the flap is tripped to dispense a dose of medicament. Dose counter 324 generally comprises a printed circuit board (PCB) and other electronic components such as an LCD to digitally display the dose count. Alternatively, a mechanical dose counter may instead be incorporated into inhaler 300 in much the same way as the inhaler disclosed in FIGS. 9-12.

FIGS. 18 through 20B illustrate another alternative embodiment of the present invention with inhaler 400 having a mechanical dose counter 420 that has a vertically mounted display wheel 422. Inhaler 400 has a load lever 402 that manually biases the fluid source 22 discharge upon downward motion.

As illustrated in FIG. 19A, fluid source 22 is retained from discharging by collapsible joint 416, which is formed by the junction of upper link 406 and lower link 408. Lower link is coupled to horizontally oriented flap 410. Inhalation forces on horn 404 cause air flow through port 412 into negative pressure chamber 414 such that a negative pressure is exerted on flap 410 to force flap 410 to rotate downward, as shown in FIG. 19B. With collapsible joint 416 away from the locked position, the fluid source is free to translate downward and discharge the medicament.

FIGS. 20A and 20B illustrate an alternative embodiment of using a dose counter 420 with a vertically oriented display wheel 422. Container sleeve 426, adapted to receive the non-dispensing end of container 22, has a plurality of protrusions 434. When the container cycles downward upon discharge, translation of the container sleeve 426 causes protrusions 434 to strike the teeth 432 of gear 424, forcing the gear 424 to rotate clockwise. The clockwise rotation of gear 424 engages vertically oriented sprocket 430 of display wheel 422, causing the display wheel 422 to turn. Sprocket 430 may be configured to engage gear 424 at specified intervals to vary the rate of rotation of the display wheel 422 with respect to the rate of rotation of the gear 424.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. An apparatus for dispensing a first fluid supplied from an external fluid source, the apparatus comprising:

a transducer adapted for receiving the first fluid from a fluid source, wherein translation of a portion of the fluid source along a first axis releases the first fluid into the transducer;

a loading member coupled to the fluid source, the loading member imposing a biasing force to the fluid source along the first axis;

a linkage coupling the transducer and the fluid source, the linkage having a collapsible joint inhibiting translation of the fluid source in the first axis when the collapsible joint is oriented in a first position, and allowing translation of the fluid source in the first axis when the collapsible joint is oriented in a second position;

wherein the linkage comprises an upper link and a lower link;

the upper link having a first end coupled to the fluid source;

the lower link having a first end coupled to the transducer;

wherein the upper link and the lower link are rotatably attached at second ends to form the collapsible joint;

wherein the collapsible joint is over-center the first axis in the first position and translates away from the first axis in the second position; and a movable member coupled to the linkage, the moveable member responsive to an inhalation force, the inhalation force causing the movable member to shift the collapsible joint from the first position to the second position, thereby allowing translation of a portion of the fluid source in the first axis from a stowed position to a discharge position to discharge the first fluid into the transducer.

2. An apparatus as in claim 1, wherein the transducer further comprises one or more slots to entrain the first fluid with a second fluid.

3. An apparatus as in claim 1, further comprising a plug coupled to the transducer, the plug retained in the first chamber of the transducer, wherein the plug has a bluff surface, the axis of the bluff surface being perpendicular to the first axis.

4. An apparatus as in claim 3, further comprising an inhalation horn coupled to the transducer, the inhalation horn having a second chamber positioned along a second axis, the second chamber in communication with the first chamber via an outlet positioned at a first end of the second chamber, wherein suction on the inhalation horn causes an inhalation force on the moveable member.

5. An apparatus as in claim 4, wherein the second axis is perpendicular to the first axis.

6. An apparatus as in claim 5, wherein the second chamber has an internal cross section that increases from the first end to a second end forming an opening in the horn.

7. An apparatus as in claim 6, wherein the internal cross section of the second chamber is parabolic.

8. An apparatus as in claim 1, wherein the moveable member comprises a flap rotatably mounted to the transducer, wherein the flap rotates in response to the inhalation force.

9. An apparatus as in claim 8, wherein the flap is configured to rotate from a first orientation retaining the collapsible joint in the first position, to a second orientation allowing the collapsible joint to move to the second position as a result of the force applied in the first axis.

10. An apparatus as in claim 9, further comprising a flap spring coupled to the flap and the transducer to return the flap from the second orientation to the first orientation after the inhalation force has subsided.

11. An apparatus as in claim 10, wherein a first end of the lower link is rotatably housed in the transducer, and a second end of the lower link is rotatably coupled to the collapsible joint to allow the collapsible joint to translate from the first position to the second position.

12. An apparatus as in claim 11, the lower link further comprising a second end coupled to the flap, the mating surfaces of the lower link and the flap configured so that the lower link contacts the flap to retain the collapsible joint in the first position when the flap is in the first orientation, and wherein the lower link is free to advance past the flap when the flap is in the second orientation to allow the collapsible joint to move to the second position.

13. An apparatus as in claim 11, further comprising a reset spring coupled to the lower link to return the collapsible joint from the second position to the first position.

14. An apparatus as in claim 11, further comprising a container holder configured to receive a first end of the fluid source, wherein the container holder is coupled to the upper link.

15. An apparatus as in claim 14, wherein the container holder further comprises one or more protrusions.

16. An apparatus as in claim 15, further comprising a dust cover pivotably coupled to the transducer, the dust cover covering the horn opening in a first orientation, and allowing access to the horn opening in a second orientation.

17. An apparatus as in claim 16, wherein the dust cover comprises one or more cams, the one or more cams configured to contact the one or more protrusions on the container holder upon rotation of the dust cover from the second orientation to the first orientation to advance the container holder and fluid source from the discharge position to the stowed position.

18. An apparatus as in claim 1, wherein the moveable member comprises a diaphragm mounted to the transducer, and wherein a central portion of the diaphragm moves in response to the inhalation force.

19. An apparatus as in claim 18, wherein the collapsible joint is coupled to the central portion of the diaphragm, and wherein the inhalation force deflects the central portion of the diaphragm to orient the collapsible joint from the first position to the second position.

20. An apparatus as in claim 1, further comprising a dose counter coupled to the fluid source, the dose counter responsive to motion of the fluid source in the first axis to count each dose of fluid released from the fluid source.

21. An apparatus as in claim 20, wherein the dose counter further comprises:
a first wheel having a plurality of teeth along its perimeter, the plurality of teeth positioned to rotationally advance the first wheel in response to movement of the fluid source along the first axis; and
a second wheel positioned adjacent the first wheel, the second wheel having markings for indicating the total number of doses discharged from the fluid source, wherein the first wheel is configured to engage the second wheel such that the second wheel rotates at a scaled movement in relation to the first wheel.

22. An apparatus as in claim 21, further comprising a sleeve configured to house a portion of the fluid source, wherein the sleeve comprises a protrusion that contacts the teeth of the first wheel to rotationally advance the first wheel as the fluid source is advanced in the first axis.

23. An apparatus as in claim 22, wherein the loading member comprises a biasing spring coupled to the sleeve, the biasing spring providing a compressive force to the fluid source to bias the fluid source to move in the first axis.

24. An apparatus as in claim 1, further comprising a manual release button, the button coupled to the collapsible joint to manually shift the collapsible joint from the first position to the second position, thereby releasing the first fluid into the transducer.

25. An inhaler for dispensing metered doses of a medicament, the inhaler comprising:
a fluid source containing the medicament, the fluid source comprising a container having a nozzle located in line with a discharge axis of the container, wherein the nozzle discharges the medicament when the container is advanced relative to the nozzle from a stowed position to a discharge position along the discharge axis;
a transducer having a surface configured to engage the nozzle of the fluid source, the surface adapted for receiving the fluid from the fluid source;
a loading member coupled to the container, the loading member imposing a biasing force to the container to discharge the container along the first axis;
a linkage coupling the transducer and the container, the linkage having a collapsible joint inhibiting translation of the container in the first axis when the collapsible joint is oriented in a first position, and allowing translation of the container in the first axis when the collapsible joint is oriented in a second position; and
a movable member coupled to the linkage, the moveable member responsive to an inhalation force, the inhalation force causing the movable member to shift the collapsible joint from the first position to the second position, thereby allowing translation of the container in the first axis from the stowed position to the discharge position to discharge the fluid into the transducer.

26. An apparatus as in claim 25, wherein the moveable member comprises a flap rotatably mounted to the transducer, wherein the flap rotates in response to the inhalation force.

27. An apparatus as in claim 26, wherein the flap is configured to rotate from a first orientation retaining the collapsible joint in the first position, to a second orientation allowing the collapsible joint to move to the second position as a result of the force applied in the first axis.

28. An apparatus as in claim 27, wherein the linkage comprises an upper link and a lower link, the upper link and the lower link rotatably attached to form the collapsible joint, a first end of the lower link rotatably housed in the transducer, a second end of the lower link rotatably coupled to the collapsible joint to allow the collapsible joint to translate from the first position to the second position.

29. An apparatus as in claim 28, the lower link further comprising a second end coupled to the flap, the mating surfaces of the lower link and the flap configured so that the lower link contacts the flap to retain the collapsible joint in the first position when the flap is in the first orientation, and wherein the lower link is free to advance past the flap when the flap is in the second orientation to allow the collapsible joint to move to the second position.

30. An apparatus as in claim 28, further comprising a container holder configured to receive a first end of the container, wherein the container holder is coupled to the upper link.

31. An apparatus as in claim 30, wherein the container holder further comprises one or more protrusions.

32. An apparatus as in claim 31, further comprising a dust cover pivotably coupled to the transducer, the dust cover covering a horn having an opening in communication with a first chamber of the transducer, the dust cover covering the horn opening in a first orientation, and allowing access to the horn opening in a second orientation.

33. An apparatus as in claim 32, wherein the dust cover comprises one or more cams, the one or more cams configured to contact the one or more protrusions on the container holder upon rotation of the dust cover from the first orientation to the second orientation to advance the container holder and container from the discharge position to the stowed position.

34. An apparatus as in claim 33, further comprising a dose counter coupled to the container, the dose counter responsive to motion of the container in the first axis to count each dose of fluid discharged from the fluid source.

35. An apparatus as in claim 34, wherein the dose counter further comprises:

a first wheel having a plurality of teeth along its perimeter, the plurality of teeth positioned to rotationally advance the first wheel in response to movement of the fluid source along the first axis; and a second wheel positioned adjacent the first wheel, the second wheel having markings for indicating the total number of doses discharged from the fluid source, wherein the first wheel is configured to engage the second wheel such that the second wheel rotates at a scaled movement in relation to the first wheel.

36. An apparatus as in claim 35, further comprising a sleeve configured to house a portion of the container, wherein the sleeve comprises a protrusion that contacts the teeth of the first wheel to rotationally advance the first wheel as the container is advanced in the first axis.

37. An apparatus as in claim 36, wherein the loading member comprises a biasing spring coupled to the sleeve, the biasing spring providing a compressive force to the container to bias the container to move in the first axis.

38. An apparatus as in claim 35, wherein the first wheel advances from the motion of the container from the stowed position to the discharge position and the motion of the container back to the stowed position.

39. An inhaler for dispensing metered doses of a medicament; the inhaler comprising:

a fluid source containing the medicament, the fluid source comprising a container having a nozzle located in line with a discharge axis of the container, wherein the nozzle discharges the medicament when the container is advanced relative to the nozzle along the discharge axis;

a container sleeve configured to house a portion of the container, the container sleeve having a protrusion extending radially from the container;

a first wheel having a plurality of individual upper and lower teeth sets along its perimeter, the plurality of upper and lower teeth positioned so that each tooth rotationally advances the first wheel in response to contact from the protrusion on the container sleeve as the container sleeve and container translates in the discharge axis; and a second wheel positioned adjacent the first wheel, the second wheel having markings solely indicating the total number of doses discharged from the fluid source, wherein the first wheel is configured to engage the second wheel such that the second wheel rotates at a scaled movement in relation to the first wheel.

40. An inhaler as in claim 39, wherein the first wheel has a plurality of engagement surfaces for engaging the second wheel, wherein the number of engagement surfaces varies the rate of the movement of the second wheel with respect to the first wheel.

41. An inhaler as in claim 39, wherein the plurality of teeth along the perimeter of the first wheel are configured to engage the container sleeve so that both upward and downward motion of the container sleeve advances the first wheel.

42. An apparatus for dispensing a first fluid supplied from an external fluid source, the apparatus comprising:

a housing adapted for receiving the first fluid from the fluid source, wherein translation of a portion of the fluid source along a first axis releases the first fluid into the housing;

a loading member coupled to the fluid source, the loading member imposing a biasing force to the fluid source along the first axis;

a linkage coupling the housing and the fluid source, the linkage having a collapsible joint inhibiting translation of the fluid source in the first axis when the collapsible joint is oriented in a first position, and allowing translation of the fluid source in the first axis when the collapsible joint is oriented in a second position;

wherein the linkage comprises an upper link and a lower link;

the upper link having a first end slideably coupled to the fluid source;

the lower link having a first end rotatably coupled to the transducer;

wherein the upper link and the lower link are rotatably attached at second ends to form the collapsible joint; and a movable member coupled to the linkage, the moveable member responsive to an inhalation force, the inhalation force causing the movable member to shift to allow translation of the collapsible joint from the first position to the second position, thereby allowing translation of a portion of the fluid source in the first axis from a stowed position to a discharge position to discharge the first fluid into the housing.

43. An apparatus as recited in claim 42, wherein the collapsible joint is configured to translate in a direction non-coincident with the first axis.

44. An apparatus as recited in claim 42:
wherein the collapsible joint is over-center with the first axis in the first position; and
wherein the collapsible joint translates away from the over-center first position to the second position not on the first axis.

45. An apparatus as recited in claim 42:
wherein, in a stowed configuration, the collapsible joint is restrained from motion by the moveably member; and
wherein in a discharge configuration, the collapsible joint is free to translate in at least one direction.

46. An apparatus as recited in claim 45, wherein, in the discharge configuration, the collapsible joint is configured to translate in a direction non-coincident with the first axis.

47. An apparatus as in claim 45:
wherein the linkage comprises an upper link and a lower link, the upper link and the lower link each having a first end that are rotatably attached to each other to form the collapsible joint;
wherein a second end of the lower link is rotatably housed in the housing; and
wherein, in the discharge configuration, the collapsible joint translates from the first position to the second position.

* * * * *